United States Patent
Kalivretenos

(10) Patent No.: US 7,229,835 B2
(45) Date of Patent: Jun. 12, 2007

(54) AMINE DETECTION METHOD AND MATERIALS

(75) Inventor: Aristotle G. Kalivretenos, Columbia, MD (US)

(73) Assignee: The University of Maryland, Baltimore County, Baltimore, MD (US)

( * ) Notice: Subject to any disclaimer, the term of this patent is extended or adjusted under 35 U.S.C. 154(b) by 897 days.

(21) Appl. No.: 09/983,743

(22) Filed: Oct. 25, 2001

(65) Prior Publication Data

US 2003/0104609 A1    Jun. 5, 2003

(51) Int. Cl.
- G01N 33/50 (2006.01)
- G01N 33/543 (2006.01)
- G01N 21/78 (2006.01)
- G01N 23/00 (2006.01)
- G01N 31/22 (2006.01)
- G01N 35/08 (2006.01)

(52) U.S. Cl. .......................... 436/111; 422/56; 422/59; 422/61; 422/69; 422/82.05; 422/82.08; 422/82.09; 436/52; 436/57; 436/86; 436/87; 436/88; 436/89; 436/90; 436/107; 436/108; 436/111; 436/112; 436/113; 436/166; 436/169; 436/172; 436/518; 436/524; 436/527; 436/528; 436/529; 436/530; 436/531; 436/532; 436/533; 436/534

(58) Field of Classification Search ............ 422/56–60, 422/68.1, 69, 82.05–82.09, 71; 436/52, 86–90, 436/57, 111–113, 164, 169–170, 172, 518, 436/524, 527, 528–534, 107–108

See application file for complete search history.

(56) References Cited

U.S. PATENT DOCUMENTS 3,725,380 A * 4/1973 Konig et al. ................ 530/341

(Continued)

FOREIGN PATENT DOCUMENTS

EP    488152    *  6/1993
WO    98/03452  *  1/1998

OTHER PUBLICATIONS

Popova, A. Doklady Bolgarskoi Akademii Nauk 1966, 19, 77-80.*
Heusel, G. et al, Angewandte Chemie 1977, 89, 681-682.*

(Continued)

Primary Examiner—Arlen Soderquist
(74) Attorney, Agent, or Firm—Rothwell, Figg, Ernst & Manbeck

(57) ABSTRACT

A compound linked to a solid support (R) through a divalent linker moiety (X) and which is represented by the following formula:

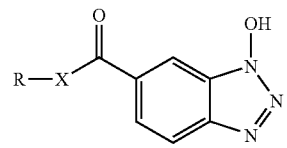

is disclosed. In particular, the 1-hydroxybenzotriazole-6-carboxylic acid is directly linked to the support under mild conditions (i.e., in aqueous or organic solvents at neutral pH and at room temperature). The polymer bound 1-hydroxybenzotriazole-6-carboxylic acid can be used for the derivatization of amines as well as for single step amino group modification of proteins, peptides, and amines via acylation or sulfonylation reactions. A flow through device and method for the single step amino group modifications of proteins, peptides, and amines is disclosed. Also disclosed is a flow through device for the detection of amines in a sample. Additionally, a device and method for the detection of amines in a sample using 1-hydroxybenzotriazole-6-carboxylic acid is disclosed. In a preferred embodiment, the device is used to detect the presence of amines in a spoiled meat product. Diagnostic kits for detecting the presence of amines is also disclosed.

49 Claims, 16 Drawing Sheets

U.S. PATENT DOCUMENTS

| | | | | | |
|---|---|---|---|---|---|
| 4,370,312 | A | * | 1/1983 | Jung et al. | 530/328 |
| 4,868,167 | A | * | 9/1989 | Mokotoff et al. | 514/176 |
| 4,923,901 | A | * | 5/1990 | Koester et al. | 521/53 |
| 5,183,740 | A | * | 2/1993 | Ligler et al. | 435/7.32 |
| 5,202,451 | A | * | 4/1993 | Fritzberg et al. | 556/419 |
| 5,204,242 | A | | 4/1993 | Junius-Comer et al. | |
| 5,403,698 | A | * | 4/1995 | Tachiki et al. | 430/286.1 |
| 5,496,700 | A | * | 3/1996 | Ligler et al. | 435/7.1 |
| 5,549,974 | A | * | 8/1996 | Holmes | 428/403 |
| 5,576,216 | A | * | 11/1996 | Patchornik | 436/86 |
| 5,585,275 | A | * | 12/1996 | Hudson et al. | 436/518 |
| 5,789,172 | A | * | 8/1998 | Still et al. | 435/6 |
| 5,917,015 | A | * | 6/1999 | Jensen et al. | 530/334 |
| 2002/0035222 | A1 | * | 3/2002 | Oh et al. | 526/261 |
| 2002/0076835 | A1 | * | 6/2002 | Ede et al. | 436/531 |

OTHER PUBLICATIONS

Moss, R. A. et al, Tetrahedron Letters 1977, 3851-3854.*
Kuzmic, P. et al, Analytical Biochemistry 1992, 205, 65-69.*
Shriver-Lake, L. C. et al, ACS Symposium Series 1996, 646(Environmental Immunochemical Methods), 46-55.*
Kunugi, S. et al, Bulletin of the Chemistry Society of Japan 1996, 69, 1747-1753.*
Charles, P. T. et al, SPIE 1997, 3105(Chemical, Biochemical, and Environmental Fiber Sensors IX), 80-87.*
Bart, J. C. et al, Sensors and Actuators B 1997, 38-39, 411-418.*
Paio, A. et al, Journal of Combinatorial Chemistry 1999, 1, 317-325.*
Piletsky, S. A. et al, Fresenius' Journal of Analytical Chemistry 1999, 364, 512-516.*
Chinchilla, R. et al, Tetrahedron Letters 2000, 41, 2463-2466.*
Yang, M. et al, Analytica Chimica Acta 2000, 409, 45-53.*
Goldstein, H. et al, Helvetica Chimica Acta 1949, 32, 2334-2339, no month.*
Nova Biochem Catalog 1999, p. 214, product No. 01-64-0179, no month.*
Chang, Y.-T. et al, Bioorganic & Medicinal Chemistry Letters 1999, 9, 2479-2482, no month.*
Lu, C. et al, Proc. China-U.S. Bilateral Symp. Polym. Chem. Phys. 1981, Meeting date 1979, 101-112.*
Berrada, A. et al, Bulletin de la Societe Chimoque de France 1989, 511-514.*
Scheuerman, R. A. et al, Tetrahedron Letters 2000, 41, 6531-6535.*
Schiemann, K. et al, Journal of Organic Chemistry 1999, 64, 4972-4975.*
Mutter, M., Tetrahedron Letters 1978, 2839-2842.*
Combs, A. P. et al, Tetrahedron Letters 1999, 40, 1623-1626.*
Rano, T.A., et al., "Solid Phase Synthesis of Aryl Ethers Via The Mitsunobu Reaction", Tetrahedron Letters, 36, 22, 3789-3792 (1995).
Deshpande, M.S., "Formation of Carbon—Carbon Bond on Solid Support: Application of the Stille Reaction", Tetrahedron Letters, 35, 31, 5613-5614 (1994).
Forman, F.W., et al., "Solid-Phase Synthesis of Biaryls via the Stille Reaction", J. Org. Chem., 60, 523-528 (1995).
Yu, K-I., et al., "Heck Reactions In Solid Phase Synthesis", Tetrahedron Letters. 35, 48, 8919-8922 (1994).
Hiroshige, M., et al., "Formation of C—C Bond In Solid Phase Synthesis Using The Heck Reaction", Tetrahedron Letters, 36, 26, 4567-4570 (1995).
Chen, C., et al., "'Analogous' Organic Synthesis of Small-Compound Libraries: Validation of Combinatorial Chemistry in Small-Molecule Synthesis", J. Am. Chem. Soc., 116,. 2661-2662 (1994).
Bunin, B.A., et al., "A General and Expedient Method for the Solid-Phase Synthesis of 1,4-Benzodiazepine Derivatives". J. Am. Chem. Soc., 114, 10997-10998 (1992).
Hobbs DeWitt, S., et al., "'Diversomers': An Approach to Nonpeptide, Nonoligomeric Chemical Diversity", Proc. Natl. Acad. Sci. USA. 90, 6909-6913 (1993).

Hobbs DeWitt, S., et al., "DIVERSOMER™ Technology: Solid Phase Synthesis, Automation, and Integration for the Generation of Chemical Diversity", Drug Development Research, 33, 116-124 (1994).
Fridkin, M., et al., "A Synthesis of Cyclic Peptides Utilizing High Molecular Weight Carriers", J. Am. Chem. Soc., 87, 20, 4645-4648 (1965).
Fridkin, M., et al., "Use of Polymers as Chemical Reagents: I. Preparation of Peptides", J. Am. Chem. Soc. 88, 13, 3164-3165 (1966).
Kalir, R., et al., "(4-Hydroxy-3-nitro)benzylated Polystyrene: An Improved Polymeric Nitrophenol Derivative for Peptide Synthesis", Eur. J. Biochem., 42, 151-156 (1974).
Laufer, D.A., et al., "A Reagent for Peptide Synthesis. Copoly(ethylene-N-hydroxymaleimide)". J. Am. Chem. Soc., 90, 10, 2696-2698 (1968).
Kalir, R., et al., "New Useful Reagents for Peptide Synthesis", Eur. J, Biochem., 59, 55-61 (1975).
Mokotoff, M., et al., "Synthesis of the C-terminal Half of Thymosin $\alpha_1$ by the Polymeric Reagent Method". Int. J. Peptide Protein Res., 21, 145-154 (1983).
Mokotoff. M., et al., "Thymosin-like Peptides as Potential Immunostimulants. Synthesis Via the Polymeric-Reagent Method", J. Med. Chem., 33, 354-360 (1990).
Weinshenker. N. M., et al., "Polymeric Reagents I. Synthesis of an Insoluble Polymeric Carbobiimide". Tetrahedron Letters. 32, 3281-3284 (1972).
Desai, M.C., et al., "Polymer Bound EDC (P-EDC): A Convenient Reagent For Formation of an Amide Bond", Tetrahedron Letters. 34, 48, 7685-7688 (1993).
Arnold, I..D., et al., "Polymer-Supported Alkyl Azodicarboxylates for Mitsunobu Reactions", J. Am. Chem. Soc., 111. 3973-3976 (1989).
Caputo, R., et al., "Polymer-Bound Triarylphospshine-Iodine Complexes. Convenient Coupling Reagent Systems in Peptide Synthesis", Synthesis, 141-143 (1995).
Pop, I.E., et al., "Versatile Acylation of N-Nucleophiles Using a New Polymer-Supported I-Hydroxybenzotriazole Derivative", J. Org. Chem., 62, 2594-2603 (1997).
Dendrinos, K., et al., "HOBT Immobilized on Macroporous Polystyrene Beads: A Useful Reagent For the Synthesis of Amides", Chem. Commun., 499-500 (1998).
Huang, W., et al., "Synthesis of Medium Ring Lactams Via Cyclization Reactions Using Polymer Bound HOBT as Catalyst", Tetrahedron Letters. 36, 50, 9113-9116 (1995).
Dendrinos, K.G., et al., "Synthesis of N-Hydroxysuccinimide Esters Using Polymer Bound HOBT", Tetrahedron Letters, 39, 1321-1324 (1998).
Dendrinos, K.G., et al., "Convenient Protection of Amines as Carbamates Using Polymer-Bound HOBT as Catalyst", J. Chem Soc., Perkin Trans., 1463-1464 (1998).
König, W., "Eine neue Methode zur Synthese von Peptiden: Aktivierung der Carboxylgruppe mit Dicyclohexycarbodiinid unter/ Zusatz von I-Hydroxy-benzotriazolen", Chem. Ber., 103, 788-798 (1970).
"Nuclear Magnetic Resonance Spectra", Sadtler Reserach Laboratories. Inc., 28971 M (1975).
Imrie, C., et al., "Photolysis of (Arylmethyl)triphenylphosphonium Salts. Substituent. Counterion, and Solvent Effects on Reaction Products", J. Org. Chem., 58, 5643-5649 (1993).
Kishikawa, K., et al., "Chemoselective Alcoholysis of Acylureas", Synthesis. 173-175 (1994).
Morcuende, A., et al., "Microwave-Promoted Transformations: Fast and Chemoselective N-Acylation of Amino Acids Alcohols Using Catalytic Amounts of Dibutyltin Oxide. Influence of the Power Output and the Nature of the Acylating Agent on the Selectivity", J. Org. Chem., 61, 5264-5270 (1996).
Kita, Y., et al., "Facile and Efficient Syntheses of Carboxylic Anhydrides and Amides Using (Trimethylsilyl)ethoxyacetylene", J. Org. Chem., 51, 4150-4158 (1986).

Richards, J.C., et al., "H NMR Spectroscopy As a Probe of the Stereochemistry of Enzymic Reactions at Prochiral Centres", Tetrahedron Letters, 39, 21, 3549-3568 (1983).

Pouchert, C.J., et al., "The Aldrich Library of $^{13}$C and $^{1}$H FT NMR Spectra, Ed. 1", Aldrich Chemical Co. (1993), p. 1385.

Seieinski, J.J., et al., "Solid-Phase Development of a 1-Hydroxybenzotriazole Linker for Heterocycle Synthesis Using Analytical Constructs". J. Combinatorial Chem., A-J (2001), 3, 387-396.

Excerpt from NOVA Biochem Products Description, Polymer-Supported Coupling Reagents, Product No. 01-64-0425 (2001).

* cited by examiner

MEMBRANE CARTRIDGE DEVICE

SENSOR APPLIED TO FRESH MEAT — WAFER IS WHITE

SENSOR ON ROTTING MEAT — AREA DIFFUSABLE TO DYE
BECOMES RED INDICATING SPOILAGE

AMINE DETECTION METHOD AND MATERIALS

BACKGROUND OF THE INVENTION

1. Field of the Invention

The present invention relates generally to polymer bound 1-hydroxybenzotriazole-6-carboxylic acid (P-HOBT) and uses thereof. In particular, the present invention relates to a device for the single-step amino group modification of proteins, peptides, and amines via acylation reactions. The present invention also relates to a method of detecting the presence of amines in a sample using polymer bound 1-hydroxybenzotriazole-6-carboxylic acid.

2. Discussion of the Background

Combinatorial chemistry has become one of the major tools in the search for new lead compounds in pharmaceutical drug discovery (1–3). As the use of combinatorial chemistry increases, much effort has gone into the development of new synthetic methods for the highly efficient preparation of chemical libraries. One of the results of this research has been an increase in the development and use of solid-phase organic synthesis techniques.

Two general protocols have been used in solid-phase organic synthesis: (i) the use of polymers as a scaffold upon which to build the desired molecule in a multi-step sequence, or (ii) the use of a polymer-supported reagent to mediate a single synthetic step. The use of polymers as templates for building complex molecules has been exploited in well-known applications such as solid-phase peptide synthesis (4) and oligonucleotide synthesis (5). Beyond these technologies, a variety of organic reactions have been successfully carried out in the solid phase (3, 5–11). Moreover, this methodology has been used for the synthesis of small heterocyclic organic molecules, including benzodiazepines, diketopiperazines and hydantoins (12–14).

Alternately, the use of polymer supported acylating agents as catalysts has been particularly useful for the formation of amide bonds, as well as ester formation. These immobilized reagents include nitrophenol (15–17), N-hydroxysuccinimide (NHS) (18), 1-hydroxybenzotriazole (HOBT) (19–21), carbodiimide (22, 23), and triphenylphosphine (24, 25). Of these polymer supported acylating agents, polymer supported HOBT (P-HOBT) has been the most useful. P-HOBT has been used as a highly reactive N-acylating agent for the formation of peptide bonds (19–21) and simple amides (26, 27). P-HOBT has also been utilized for the synthesis of medium-ring lactams from linear ω-amino acid precursors (28), as an acylating agent for the synthesis of NHS esters (29), and for the carbamate protection of primary and secondary amines (30). Excluding solid-phase peptide synthesis and organic synthesis, current protein, peptide, and amine modifications are carried out in solution phase reactions which involves subsequent work-up and/or purification of the product after the reaction.

In the work of Fridkin and Patrchornik (19), the immobilized HOBT reagent was synthesized by the direct functionalization of polystyrene utilizing 4-chloro-3-nitrobenzyl alcohol under Friedel-Crafts conditions. The HOBT moiety was formed by treatment of the polymer with hydrazine monohydrate and subsequent cyclization under acidic conditions using known methods (31). Although this method has been utilized for the preparation of P-HOBT, it is limited to polystyrene (aryl) based polymers, and is not always reproducible due to the Friedel-Crafts reaction, the synthesis of P-HOBT was improved by the initial coupling of 4-chloro-3-nitrobenzenesulfonyl chloride to an aminomethylated polystyrene polymer, followed by reaction with hydrazine monohydrate and cyclization under acidic conditions (26). The polymer is highly active due to the presence of the electron withdrawing sulfonyl group in the benzene ring, and can be synthesized in a reproducible manner. A disadvantage of this approach is the two step method of HOBT cyclization after addition of the sulfonyl chloride to the polymer, utilizing conditions which may not be compatible for the derivatization of all solid supports. This limits the choice of solid supports used to immobilize the HOBT and requires the adaptation of an application to utilize a polymer support that can be modified using the heretofore known method of coupling 4-chloro-3-nitrobenzoic acid to the polymeric support, followed by the two step formation of HOBT.

Thus, before the present invention, there were no known effective means of directly immobilizing 1-hydroxybenzotriazole or a derivative thereof to a solid support under mild conditions, i.e., in organic or aqueous solvents at neutral pH and at room temperature. Additionally, there were no known methods of using immobilized 1-hydroxybenzotriazole or derivatives thereof for self-contained, single step modifications of amino groups on proteins, peptides, and amines, or to using 1-hydroxybenzotriazole-6-carboxylic acid to effectively and efficiently detect the presence of amines in a sample.

SUMMARY OF THE INVENTION

It is an object of the present invention to provide 1-hydroxybenzotriazole-6-carboxylic acid linked to a solid support.

It is another object of the present invention to provide a flow-through device for the one-step modification of proteins, peptides, and amino groups via acylation reactions.

It is yet another object of the present invention to provide a method of detecting the presence of amines in a sample.

It is a further object of the present invention to provide a device for detecting the presence of amines in a sample.

It is another object of the present invention to provide a flow-through device to detect the presence of amines.

It is yet another object of the present invention to provide a diagnostic kit to indicate the spoilage of food products.

It is a further object of the present invention to provide a meat packaging sensor to indicate the spoilage of food products.

With the foregoing and other objects, advantages and features of the invention that will become hereinafter apparent, the nature of the invention may be more clearly understood by reference to the following detailed description of the preferred embodiments of the invention and to the appended claims.

DESCRIPTION OF THE PREFERRED EMBODIMENTS

Figure 1:
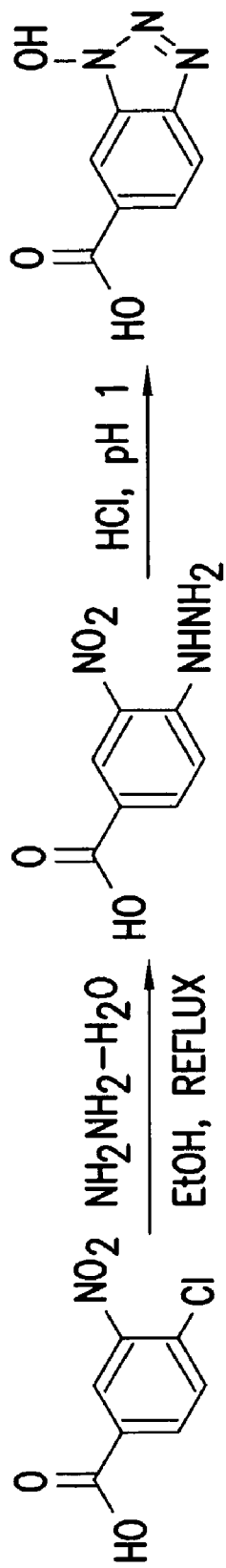
FIG. 1 is a schematic of the two step formation of 1-hydroxybenzotriazole-6-carboxylic acid.

Referring to FIG. 1, 1-hydroxybenzotriazole-6-carboxylic acid is formed in two steps from 4-chloro-3-nitrobenzoic acid. In the first step, 4-chloro-3-nitrobenzoic acid and hydrazine monohydrate are heated at reflux in ethanol to yield a crude precipitate. In the second step, the crude precipitate is dissolved in water and acidified with HCl to pH 1 to yield 1-hydroxybenzotriazole, a peach colored precipitate. Confirmation of the compound can be conducted by NMR spectroscopy and high resolution mass spectroscopy (HRMS), as well as other detection methods determined by one of skill in the art.

Current methods for the preparation of polymer supported 1-hydroxybenzotriazole ("P-HOBT") rely on the ability to incorporate a derivative of 4-chloro-3-nitrobenzoic acid on the polymeric support, followed by the addition of hydrazine to the polymer in ethanol at reflux (80° C.) and subsequent cyclization under acidic conditions (e.g., HCl, pH 1) to yield the 1-hydroxybenzotriazole moiety. This approach is disadvantageous in that the two step process for HOBT cyclization after the addition of 4-chloro-3-nitrobenzoic acid to the polymer limits the choice of solid supports used to immobilize the HOBT moiety.

On the other hand, 1-hydroxybenzotriazole-6-carboxylic acid has the ability to link directly to a solid support under very mild conditions. The phrase "mild conditions" as used herein indicates that the reactions are run in organic or aqueous solvents at neutral pH and at room temperature. The use of 1-hydroxybenzotriazole-6-carboxylic acid greatly expands the choice of supports from that which can be utilized when HOBT alone is linked to a support.

Furthermore, 1-hydroxybenzotriazole-6-carboxylic acid can be used for the efficient and easy immobilization of the HOBT moiety on solid supports that contain amino groups, hydroxyl groups, or other functional groups known to one of skill in the art to form stable adducts upon reaction with a carboxylic acid under mild conditions. For example, by linking the 1-hydroxybenzotriazole-6-carboxylic acid directly to a solid support with an amino group, the HOBT moiety is coupled to the solid support through an electron withdrawing amide linkage. As a result, the reactivity of HOBT as an acylating agent is increased.

Alternatively, derivatives of 1-hydroxybenzotriazole-6-carboxylic acid modified at the carboxylate moiety to include another functionality such as a sulfhydryl group may be used to link the HOBT moiety to a solid support. Additionally, 1-hydroxybenzotriazole-6-carboxylic acid and derivatives thereof at the carboxylate moiety can also be used to incorporate 1-hydroxybenzotriazole functionality in other organic molecules that are not polymer based.

Figure 2:
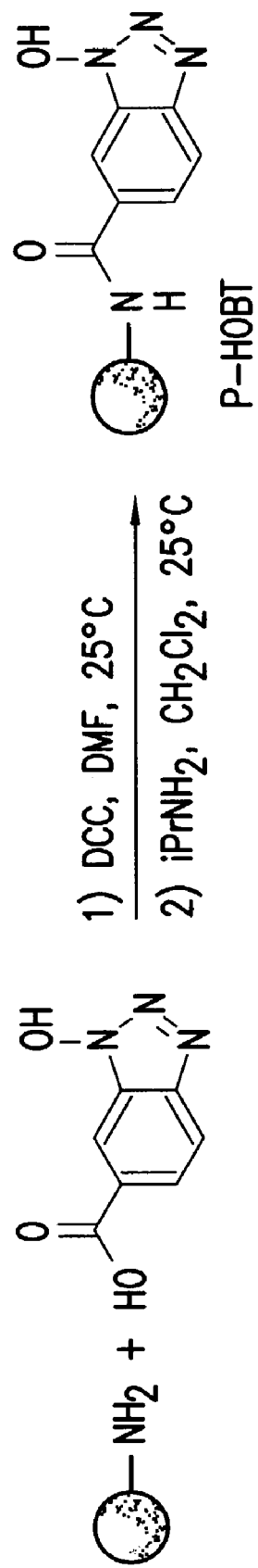
FIG. 2 is a schematic of the single step formation of polymer bound 1-hydroxybenzotriazole-6-carboxylic acid.
Figure 3A:
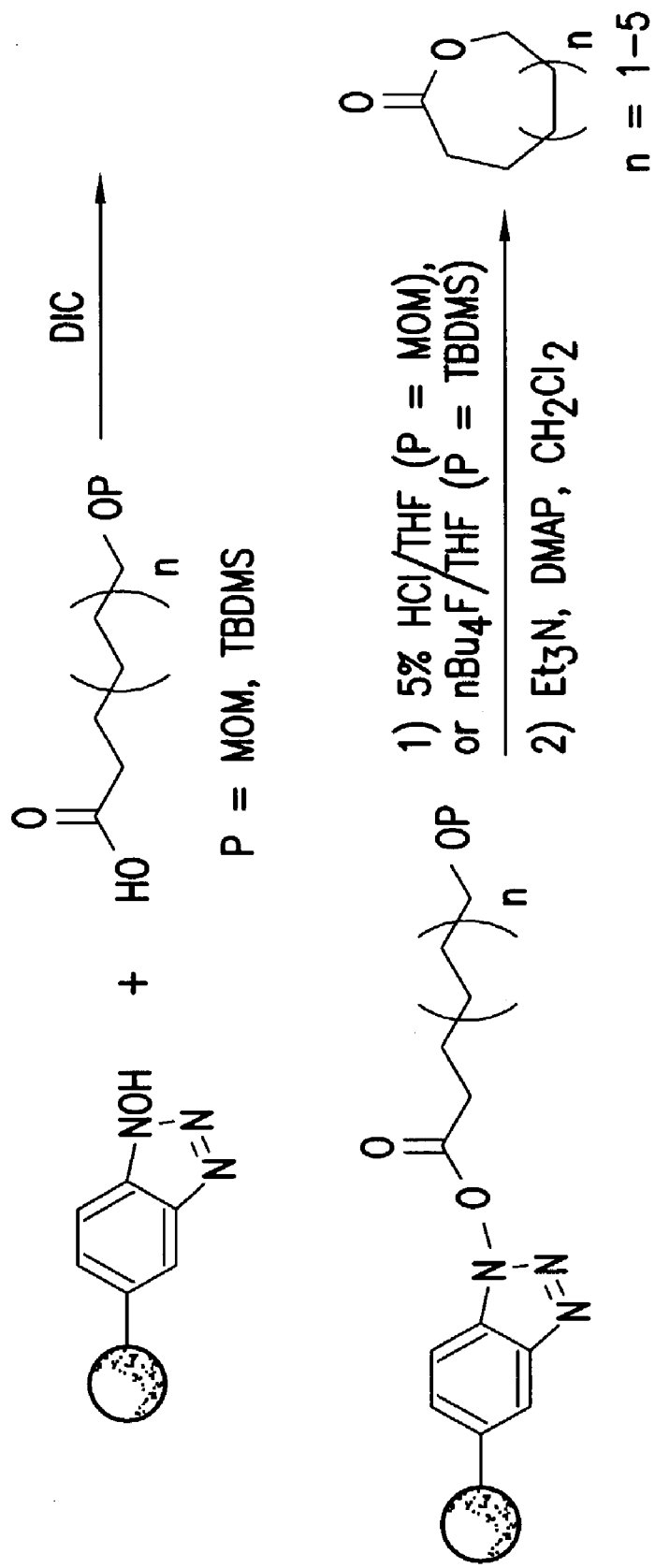
FIGS. 3a–3f are schematics of general reactions for the formation of lactones, amides, lactams, carbamates, esters, and sulfonamides using polymer bound 1-hydroxybenzotriazole-6-carboxylic acid.
Figure 3B:
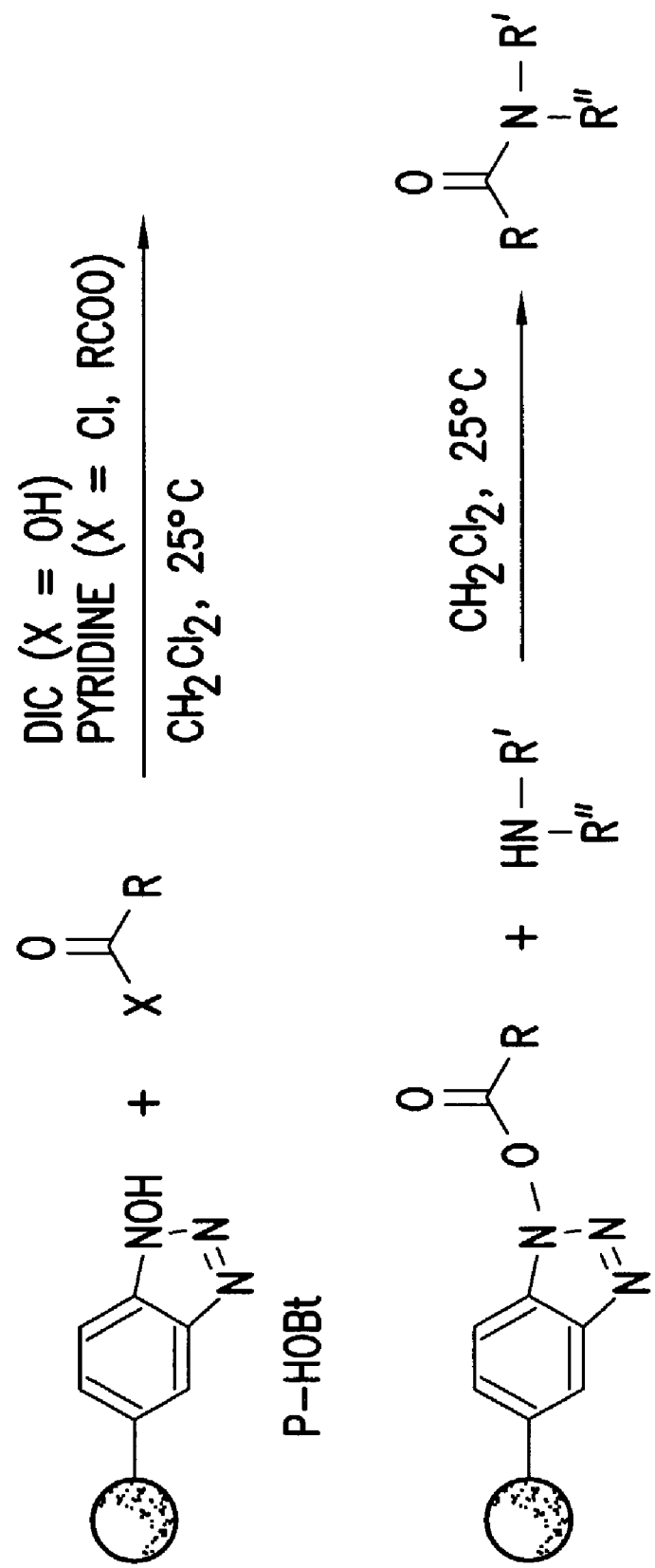
Figure 3C:
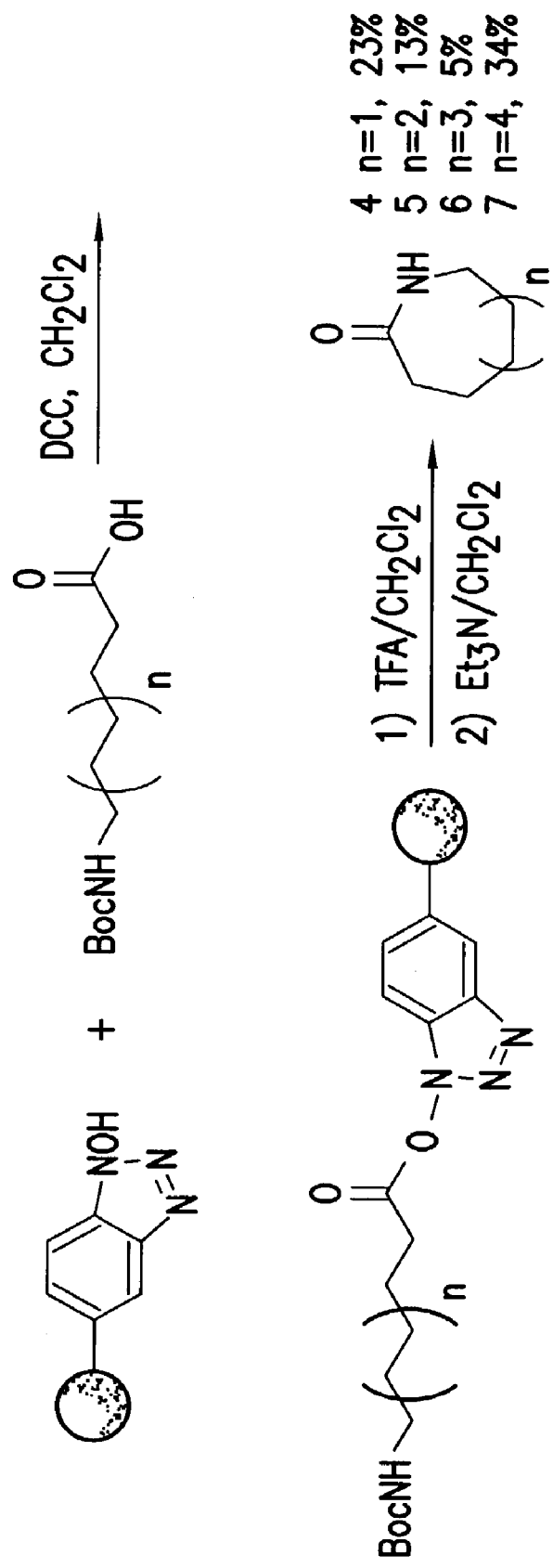
Figure 3D:
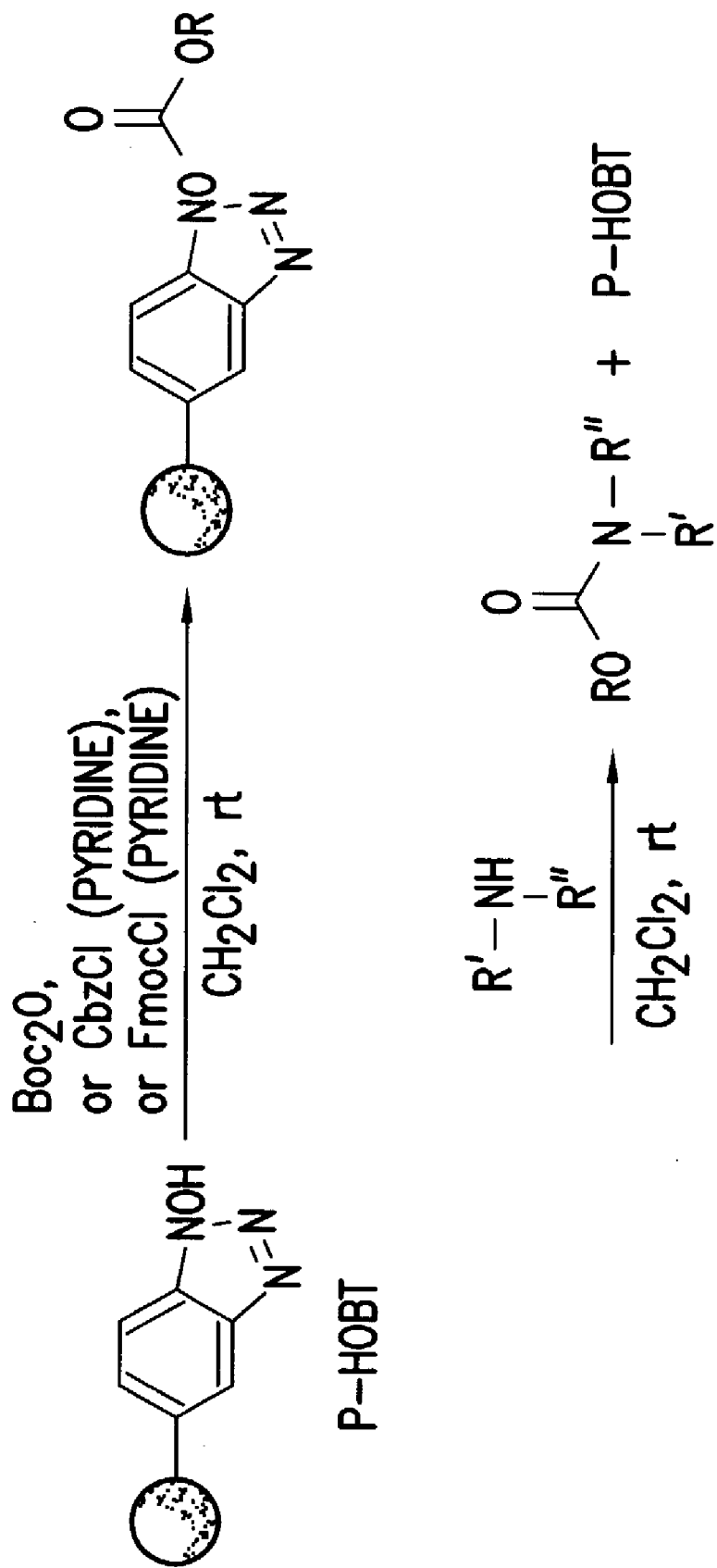
Figure 3E:
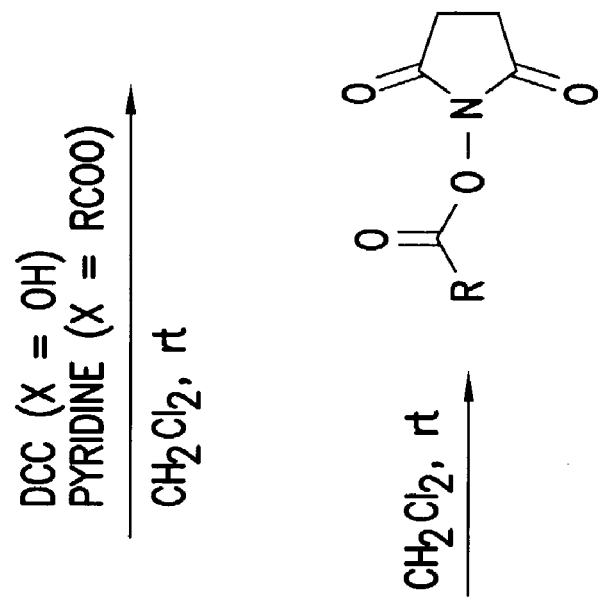
Figure 3E:
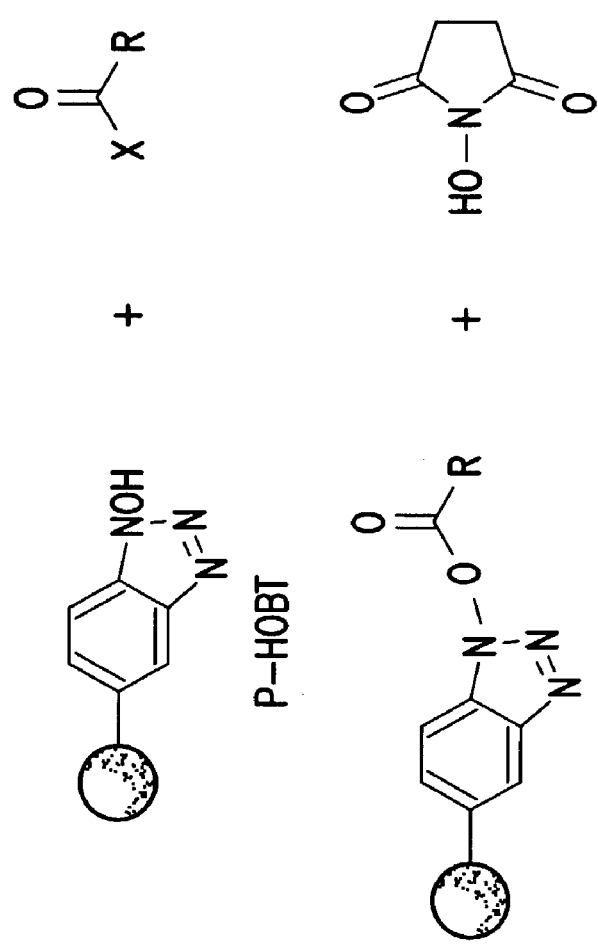
Figure 3F:
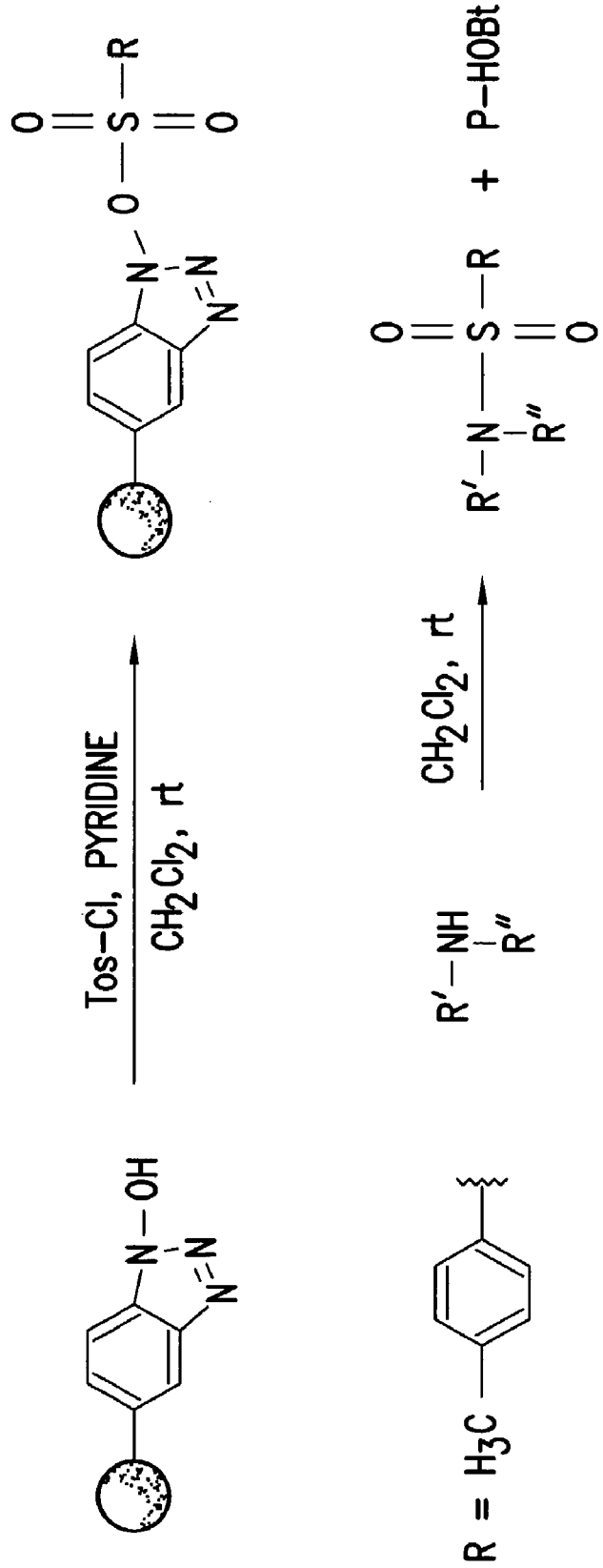

The single step linking of the 1-hydroxybenzotriazole-6-carboxylic acid to a polymer is shown in FIG. 2. As shown in FIG. 2, the aminoalkylated polymer is first suspended in N,N-dimethylformamide (DMF). 1-hydroxybenzotriazole-6-carboxylic acid and dicyclohexylcarbodiimide (DCC) or diisopropylcarbodiimide (DIC) is then added to the polymer suspension. After the reaction is complete, the polymer bound HOBT is filtered and washed using DMF, dichloromethane ($CH_2Cl_2$), and methanol (MeOH). The derivatized polymer is treated with a large excess of isopropylamine, followed by rigorous washing to provide the free HOBT reagent. The polymer supported HOBT retains its high reactivity, and the resulting electron withdrawing amide linkage enhances the reactivity of the immobilized HOBT moiety as a leaving group.

The choice of solid supports depends on the desired chemistry to be attempted with the polymer bound 1-hydroxybenzotriazole-6-carboxylic acid. For example, the use of the HOBT moiety immobilized on Merrifield type polystyrene (PS) resins, whose degree of swelling varies greatly depending on the solvent, would be appropriate for reactions in organic solvents, but would not be appropriate under aqueous conditions. For the derivatization of peptides or proteins, a solid support which has the ability to be used in aqueous and organic solvents without swelling or contraction is desirable. Polystyrene and polystyrene/polyethylene glycol polymers are limited to reactions in organic solvents due to their poor and limited swelling properties in water. Additionally, silica and glass bead based solid supports can be used in aqueous or organic solvents without swelling or contraction. Supports suitable for the immobilization of the 1-hydroxybenzotriazole-6-carboxylic acid would be easily identified by one of skill in the art and include supports such as polystyrene, polystyrene/polyethylene glycol graft copolymers, silica gels, controlled pore glass, agarose, sepharose, silica beads and glass beads.

Immobilized 1-hydroxybenzotriazole-6-carboxylic acid can be used in liquid chromatography for the derivatization (on-line and off-line) of naturally occurring amines for improved separation and identification properties. Amines are widely found in nature. For example, biogenic amines are present in living cells and in food products. A number of naturally occurring primary and secondary amines can be found in meat and fish as it spoils (e.g., histamine, putrescine, cadaverine, methyl amine), tobacco smoke (e.g., methylamine, dimethylamine, pyrrolidine), and beer (e.g., ethylamine, isoamylamine, dibutylamine). Coniine (i.e., 2-propylpiperidine, hemlock poison) is a simple non-chromophoric cyclic amine compound. Other naturally occurring, non-chromophoric amines include glucosamine, galactosamine, mannosamine, and heparin. Although amines are generally easy to separate, the lack of a chromophore in their structure makes amines difficult to detect. To overcome this problem, P-HOBT is used for the one-step derivitization of amines with a detectable agent, including, but not limited to, chromophoric agents (e.g., FD&C Red 3 or an azo dye such as DABCYL or DABSYL), fluorogenic agents (e.g., pyrene, fluorescein, lucifer yellow, BODIPY, rhodamine, DANSYL, EDANS, or derivatives thereof), radioactive agents (e.g., $^3H$, $^{14}C$, $^{125}I$, $^{35}S$, or $^{32}P$), and electrochemical active agents which may include a thiol or catechol moiety. The derivatization may occur in an aqueous environment or in an organic solvent. The one-step derivatization of amines with chromophoric or fluorogenic agents using P-HOBT allows for the specific and sensitive determination of amines, such as with UV/Vis and fluorescence detection.

Additionally, immobilized 1-hydroxybenzotriazole-6-carboxylic acid can be used for amino group modifications of proteins, peptides, and amines via acylation and sulfonylation reactions in either organic or aqueous environments. These modifications include the formation of amides, carbamates, and sulfonamides. Moreover, immobilized 1-hydroxybenzotriazole-6-carboxylic acid can be used for the modification of amines to lactams, and the conversion of hydroxyl groups to esters and lactones. General reactions for the formation of lactones, amides, lactams, carbamates, esters, and sulfonamides using polymer bound 1-hydroxybenzotriazole-6-carboxylic acid are shown in FIGS. 3a–3f. Applications of these chemistries include radiolabeling (e.g., $^{125}I$, $^3H$, $^{14}C$, $^{35}S$, or $^{32}P$) chromophoric labeling, fluorescent labeling, affinity labeling (e.g., biotin), activation for covalent crosslinking (e.g., maleimido or azido group), and amine protection as carbamates (e.g., Fmoc, Cbz, Boc) or sulfonamides (e.g., tosylates). P-HOBT is ideally suited for this type of chemistry since the derivatizing reagent is immobilized, and once the reaction is complete, all that exists in the solution is the product.

Figure 4:
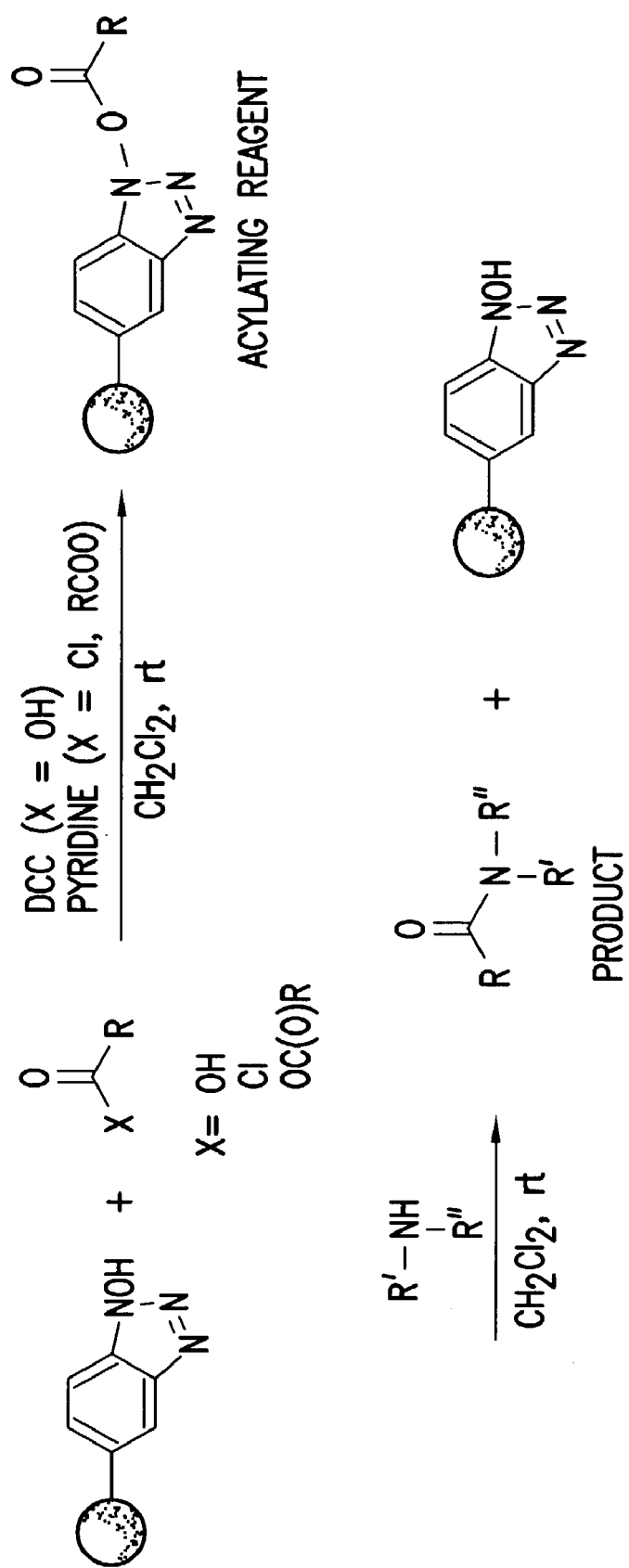
FIG. 4 is a schematic of a general acylation reaction using polymer bound 1-hydroxybenzotriazole-6-carboxylic acid.

The general acylation reaction for polymer bound 1-hydroxybenzotriazole-6-carboxylic acid is shown in FIG. 4. For ease of synthesis and potential automation, acylation reactions are typically carried out in 8 ml Extract-Clean™ solid phase extraction tubes equipped with a disposable inlet cap and a one-way stopcock on the outlet. Reactions are mixed by gentle rocking and filtration is carried out using a 12-port solid phase extraction manifold connected to a water aspirator. Initially, the polymer-bound ester (R=alkyl, aryl) or carbonate (R=alkoxy) is formed by the addition of the acid anhydride, acid chloride or the desired chloroformate reagent and pyridine to the immobilized HOBT group, or by coupling the free carboxylic acid to the polymer using DCC or DIC as a catalyst. After washing the activated resin thoroughly to remove side products, the resin is suspended in solvent containing 0.8 equivalents of amine (or other nucleophile) based on polymer activity. The reaction mixture is then rocked at room temperature. Filtration and subsequent concentration of the filtrate yields the desired product. The recovered polymer bound HOBT is fully recoverable and recyclable.

The general sulfonylation reaction for polymer bound 1-hydroxybenzotriazole-6-carboxylic acid is carried out in an analogous fashion to the acylation reaction. For ease of synthesis and potential automation, sulfonylation reactions are typically carried out in 8 ml Extract-Clean™ solid phase extraction tubes equipped with a disposable inlet cap and a one way stopcock on the outlet. Reactions are mixed by gentle rocking and filtration is carried out using a 12-port solid phase extraction manifold connected to a water aspirator. Initially, the polymer-bound sulfonate ester (R=alkyl, aryl) is formed by the addition of the sulfonyl chloride and pyridine to the immobilized HOBT group. After washing the activated resin thoroughly to remove side products, the resin is suspended in solvent containing 0.75 equivalents of amine based on polymer activity. The reaction mixture is then rocked at room temperature. Filtration and subsequent concentration of the filtrate yields the desired product. The recovered polymer bound HOBT is fully recoverable and recyclable.

Figure 5A:
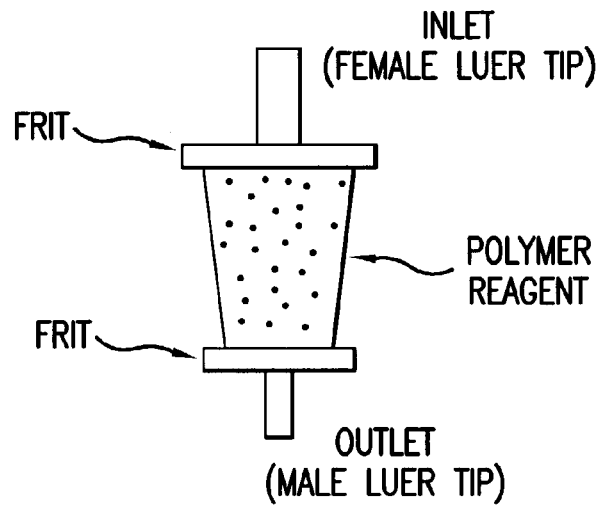
FIG. 5a is an illustration of a flow-through cartridge device according to one embodiment of the present invention.
Figure 5B:
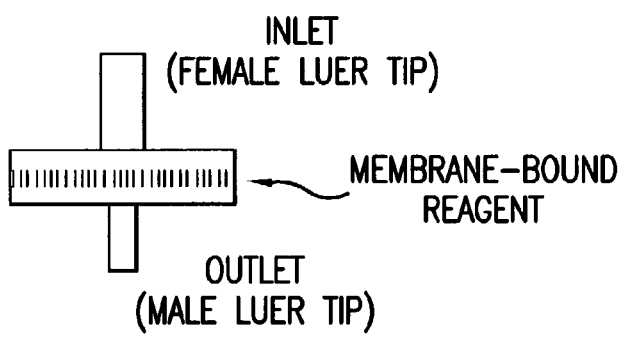
FIG. 5b is an illustration of flow-through membrane device according to one embodiment of the present invention.
Figure 5C:
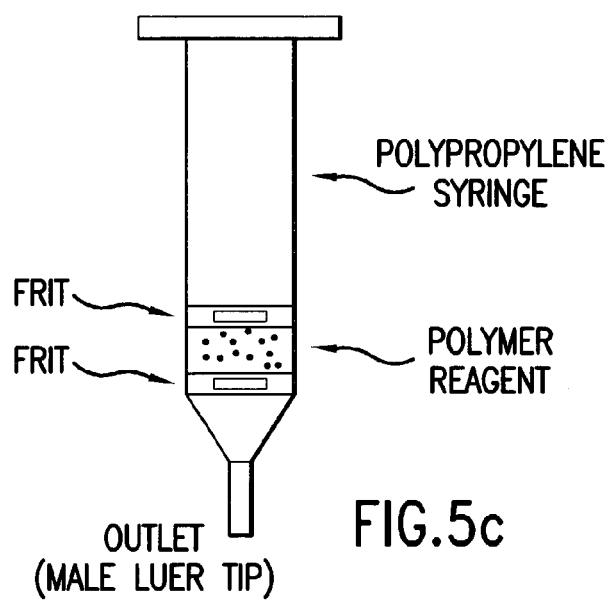
FIG. 5c is an illustration of a flow-through syringe device according to one embodiment of the present invention.

The immobilized HOBT can be used for amino group modification of proteins, peptides, and amines via acylation reactions and sulfonylation reactions such as in batch reactions or in a flow-through device such as a cartridge containing a polymer-bound reagent (FIG. 5a) or membrane-bound reagent (FIG. 5b), syringe device (FIG. 5c), or column (not shown). The flow through device is not limited, and includes other flow through devices readily determined by one of skill in the art. A variety of modifications may be performed depending on the acylating agent used, including radiolabeling, chromophoric labeling, fluorescent labeling, affinity labeling, activation for covalent crosslinking, and amine protection. The immobilized HOBT can be used to modify amines with a detectable agent such as a chromophoric agent, a fluorogenic agent, a radioactive agent, or an electrochemical agent. Suitable examples of detectable agents are set forth above, but would easily be determined by one of skill in the art. In general, the polymer bound 1-hydroxybenzotriazole-6-carboxylic acid is self-contained in a prepackaged, single use, readily disposable flow-through device. The flow-through device can be prepared from microgram to multi-gram scale (e.g., up to 10 g.).

In one embodiment, the polymer bound 1-hydroxybenzotriazole-6-carboxylic acid is pre-packaged in a flow-through polypropylene cartridge with the inlet designed for the attachment of a luer tip/syringe device and the outlet is either designed for attachment to a luer tip or is a luer tip. Preferably, the 1-hydroxybenzotriazole-6-carboxylic acid is linked to a solid support. Examples of suitable supports include polystyrene, polystyrene/polyethylene glycol graft copolymer, silica gel, controlled pore glass, agarose, sepharose, a solid polymer having a primary amine, a solid polymer having a secondary amine, cellulose, cellulose acetate, polypropylene, polyurethane, chitosan, polyacrylonitrile, polysulfone, and polyvinyl alcohol. A luer tip syringe (e.g., a 2.5 ml polypropylene syringe) is attached to the inlet.

Preparation of the device for reaction occurs by wetting the device with the desired solvent using the syringe. The substrate to be modified is diluted in the wetting solvent and is then added to the device through the syringe. Acylation takes place by allowing the substrate solution to pass through the device into a collection vessel which can be attached directly to the device or placed below the device. The substrate can pass through the device by gravity, it can be forced through the device such as by with the syringe plunger, or it can be pulled through by the application of vacuum to the outlet. The modified substrate can be utilized as is as it exits the device, or it can be isolated by removal of the solvent. Once used, the device is thrown away. Thus, there is provided a means for a single-step modification of the protein/peptide/amine group via an acylation or sulfonylation reaction. Since no soluble reagents are added to the substrate solution, no purification is required. The advantages of such a device include ease of use, facile disposal of spent reagent (i.e., the cartridge can be thrown away intact), no work-up or product purification needed, cartridges can be prepared from microgram to gram scale, minimal amounts of solvent are needed, and the device is cost effective.

Not only can polymer bound 1-hydroxybenzotriazole-6-carboxylic acid be used for acylation reactions, etc., it can be used to detect amines in a sample via amide derivatization. In one embodiment, the polymer bound 1-hydroxybenzotriazole-6-carboxylic acid bears a dye, or a specific color or signal, as an activated ester or sulfonate ester. Other linkages and indicators can be easily determined by one of skill in the art, and are within the scope of the present invention. The HOBT bearing the color indicator or signal is bound to a porous membrane which allows the unrestricted passage of amines. The 1-hydroxybenzotriazole-6-carboxylic acid can be bound to the membrane by amide bond formation or can be directly bound via an ester linkage. Underlaying the HOBT bound membrane is a porous membrane having a pre-designated molecular weight cutoff (MWCO) which permits small molecules such as amines to pass, but will not allow intact cells, proteins, or other contaminants to pass.

Overlaying this amine-passing membrane layer is a coating through which unbound dye may diffuse. This coating layer may be overlayed with a masking layer, which limits the portions of the coating layer that are visible to the naked eye. When amines are free in the sample, they pass through the porous membrane and react with the immobilized 1-hydroxybenzotriazole-6-carboxylic acid, causing the release of the dye. The dye then diffuses through the coating layer located over the amine-passing membrane, causing a color change on the coating layer on any portion not covered by the masking layer, thus indicating the presence of amines. The intensity of the color change is proportional to the total amine concentration in the sample.

In another embodiment, the polymer bound 1-hydroxybenzotriazole-6-carboxylic acid bears a dye, or a specific color or signal, as an activated ester or sulfonate ester. Other linkages and indicators can be easily determined by one of skill in the art, and are within the scope of the present invention. The HOBT bearing the dye, color indicator, or signal is bound to a solid support which is further contained in a porous bag (e.g., tea bag) or in a porous, but rigid material (e.g., test strip). The 1-hydroxybenzotriazole-6-carboxylic acid can be bound to the solid support by amide bond formation. The "tea bag" or "test strip" HOBT reagent is contained in a transparent reaction vessel (e.g., test tube, or cuvette) to which is added reaction media (buffer) suitable for the efficient acylation/sulfonylation of amines by HOBT.

After a sample containing amines is added to the reaction vessel, the reaction vessel is closed and agitated. During agitation, the sample passes through the "tea bag" or "test strip" and free amines present in the sample react with the immobilized 1-hydroxybenzotriazole-6-carboxylic acid, releasing the dye. The dye then diffuses into the bulk solution, causing a color change throughout the reaction vessel, thereby indicating the presence of amines. The HOBT reagent may then be removed from the reaction vessel to stop any further reaction from occurring. The intensity of the color change is proportional to the total amine concentration in the sample, providing a qualitative analysis for amine content. An aliquot of the buffer solution may be further analyzed by known techniques (e.g., high performance liquid chromatography) for quantitative identification of the structure and concentration profile of the amines present in the sample.

Having generally described this invention, a further understanding can be obtained by reference to certain specific examples which are provided herein for purposes of illustration only and are not intended to be limiting unless otherwise specified.

EXAMPLES

1. Preparation of Polymer-Supported HOBT

Formation of 1-hydroxybenzotriazole-6-carboxylic acid

A solution of 4-chloro-3-nitrobenzoic acid (5.047 g, 25.60 mmol) and hydrazine monohydrate (25 ml) in 250 ml of 95% ethanol was heated at reflux for 5.5 hours. At this time, the solution turned dark orange and a precipitate formed. The suspension was then cooled to 25° C. and filtered. Next, the orange precipitate was washed with cold ethanol. The precipitate was dissolved in 500 ml of water and the pH was adjusted to 1 using concentrated HCl. A peach colored precipitate formed during this time. The precipitate was collected by filtration, washed with water, and dried in vacuo to yield 3.153 g (69%).

$^1$H NMR: (300 MHz, DMSO-$d_6$) ä 7.92 (dd, 1H, J=0.9, 8.7 Hz, ArH$_6$), 8.07 (d, 1H, J=8.7 Hz, ArH$_5$), 8.23 (s, 1H, Ar H$_8$), 13.6 (bs, 1H, COOH); $^{13}$C NMR: (CDCl$_3$) ä 111.23, 112.354, 119.79, 118.77, 124.35, 125.33, 127.60, 129.70, 144.54, 166.; HRMS calculated for $C_7H_6O_3N_3$ 180.04091 [M+1]$^+$, found 180.04041 [M+1]$^+$.

Polymer-Supported 1-hydroxnbenzotriazole (P-HOBT 1)

Aminomethyl polystyrene (0.5010 g, 0.90 mmol/g NH$_2$, 0.451 mmol, Sigma, 1% DVB crosslinked, 200–400 mesh) was washed with DMF (3×5 ml), MeOH (3×5 ml) and DMF (3×5 ml). The polymer was suspended in DMF and 0.2418 g (1.350 mmol, 2.99 equiv) of 1-hydroxybenzotriazole-6-carboxylic acid was added. The suspension was rocked for 10 minutes. DCC (0.2968 g, 1.438 mmol, 3.19 equiv) was then added. The suspension was subsequently stirred for 1.25 hours. At this time, the polymer was filtered with DMF (3×5 ml), CH$_2$Cl$_2$ (3×5 ml), DMF (3×5 ml), MeOH (3×5 ml), DMF (3×5 ml) and MeOH (3×5 ml), and aspirated for 15 minutes. The crude activated polymer was then suspended in CH$_2$Cl$_2$ and isopropylamine (0.26 g, 0.38 ml, 4.4 mmol) was added. The suspension was rocked for 1.25 hours, filtered with DMF (3×5 ml), CH$_2$Cl$_2$ (3×5 ml), DMF (3×5 ml) and MeOH (3×5 ml), and aspirated for 15 minutes to yield 0.569 g of P-HOBT.

Assay of hydroxyl group content in P-HOBT 1

Acetic anhydride (0.206 g, 0.190 ml, 2.02 mmol) and pyridine (0.235 g, 0.240 ml, 2.97 mmol) was added to a suspension of P-HOBT (0.506 g) in CH$_2$Cl$_2$ (5 ml). The suspension was subsequently rocked for 30 minutes at 25° C. The polymer was then filtered and washed with CH$_2$Cl$_2$ (3×5 ml), DMF (3×5 ml), CH$_2$Cl$_2$ (3×5 ml), and anhydrous Et$_2$O (3×5 ml). The polymer was resuspended in CH$_2$Cl$_2$ (5 ml) and isopropylamine (0.278 g, 0.400 ml, 4.70 mmol) was added. Next, the suspension was rocked at 25° C. for 4 hours. The polymer was then filtered and washed with CH$_2$Cl$_2$ (4×5 ml). The filtrate and washings were combined and concentrated to yield 0.0121 g n-isopropyl acetamide as a clear oil. This gave an activity of 0.592 mmol/g for P-HOBT.

$^1$H NMR (300 MHz, CDCl$_3$): ä 1.15 (d, 6H, J=9.0 Hz, CH (CH$_3$)$_2$), 1.95 (s, 3H,CH$_3$CO), 4.03–4.08 (m, 1H, J=7.2 Hz (CH$_3$)$_2$CH), 5.45 (bs, 1H, NH); $^{13}$C NMR (CDCl$_3$): ä 22.74 (C(CH$_3$)$_2$), 23.49 (CH$_3$CO), 41.35 (C(CH$_3$)$_2$), 169.13 (CH$_3$ CO).

P-HOBT on other solid supports

The method above was used to prepare P-HOBT on a variety of solid supports as shown in Table 1.

TABLE 1

P-HOBT Activity

| P-HOBT | Polymer | —NH$_2$ activity | HOBT activity |
|---|---|---|---|
| 1 | Aminomethyl polystyrene (1% DVB crosslinked, 200–400 mesh, Sigma Chemical Co.) | 0.9 mmol/g | 0.59 mmol/g |
| 2 | ArgoGel-NH$_2$ (120–230 mm, Argonaut Technologies, Inc.) | 0.42 mmol/g | 0.25 mmol/g |
| 3 | ArgoGel-NH$_2$ (120–230 mm, Argonaut Technologies, Inc.) | 0.42 mmol/g | 0.39 mmo/g |
| 4 | 3-aminopropyl silica gel (Aldrich Chemical Co.) | ≦1 mmol/g | 0.45 mmol/g |
| 5 | 3-aminopropyl silica gel (Aldrich Chemical Co.) | ≦1 mmol/g | 0.45 mmol/g |
| 6 | 3-aminopropyl silica gel (Aldrich Chemical Co.) | ≦1 mmol/g | 0.49 mmol/g |
| 7 | aminopropyl controlled pore glass beads (170Å, 200–400 mesh, Sigma Chemical Co.) | 0.14 mmo/g | 0.13 mmol/g |
| 8 | 3-aminopropyl controlled pore glass beads (350Å, 200–400 mesh. CPG, Inc.) | 0.57 mmol/g | 0.145 mmol/g |

TABLE 1-continued

P-HOBT Activity

| P-HOBT | Polymer | —NH$_2$ activity | HOBT activity |
|---|---|---|---|
| 9 | 3-aminopropyl controlled pore glass beads (350Å, 200–400 mesh. CPG, Inc.) | 0.57 mmol/g | 0.135 mmol/g |

All acylation and sulfonylation reactions utilizing P-HOBT were carried out in 8 mL or 8 mL Extract-Clean™ solid phase extraction tubes (from Alltech Associates, Inc.) equipped with a disposable inlet cap and a one-way stopcock on the outlet. Reactions were mixed by gentle rocking. Filtration was carried out using a 12-port solid phase extraction manifold connected to a water aspirator.

2. Amide Formation Using P-HOBT

N-benzylacetamide

To a suspension of P-HOBT 1 (0.212 g, 0.125 mmol) in CH$_2$Cl$_2$ (5 mL) was added acetic anhydride (0.216 g, 0.200 mL, 2.12 mmol, 17 equiv.) and pyridine (0.234 g, 0.240 mL, 2.96 mmol, 24 equiv.). The suspension was subsequently rocked for 60 minutes at 25° C. The polymer was then filtered and washed with CH$_2$Cl$_2$ (3×5 mL), NMP (3×5 mL), CH$_2$Cl$_2$ (3×5 mL), and anhydrous Et$_2$O (3×5 mL). The polymer was re-suspended in CH$_2$Cl$_2$ (5 mL) and benzylamine (0.0098 g, 0.010 mL, 0.91 mmol, 0.73 equiv. based on P-HOBT) was added. The suspension was rocked at 25° C. for 4 h. The polymer was then filtered and washed with CH$_2$Cl$_2$ (4×5 mL). The filtrate and washings were combined and concentrated to yield 0.014 g (100%) of N-benzylacetamide as a white solid.

$^1$H NMR (300 MHz, CDCl$_3$): δ 2.01 (s, 3H, C(O)CH$_3$), 4.41 (s, 1H, ArCH), 4.42 (s, 1H, ArCH), 5.90 (bs, 1H, NH), 7.29 (m, 5H, ArH); LRMS calculated for C$_9$H$_{11}$NO [M$^+$] 149, found [M$^+$] 149.

3. Carbamate Formation Using P-HOBT

N-FMOC-benzylamine

To a suspension of P-HOBT 5 (1.0 g, 0.49 mmol) in CH$_2$Cl$_2$ (5 mL) was added fluorenylmethoxychyloroformate (0.350 g, 1.35 mmol, 3.0 equiv.) and pyridine (0.147 g, 0.150 mL, 1.86 mmol, 4.1 equiv.). The suspension was subsequently rocked for 60 minutes at 25° C. The polymer was then filtered and washed with CH$_2$Cl$_2$ (3×5 mL), MeCN (3×5 mL), and MeOH (3×5 mL). The polymer was re-suspended in CH$_2$Cl$_2$ (5 mL), followed by the addition of benzylamine (0.036g, 0.037 mL, 0.34 mmol, 0.75 equiv. based on P-HOBT 5). The suspension was rocked at 25° C. for 22 h. The polymer was then filtered and washed with CH$_2$Cl$_2$ (2×5 mL). The filtrate and washings were combined and concentrated to yield 0.084 g (76%) of N-FMOC-benzylamine as a solid.

LRMS calculated for C$_{19}$H$_{22}$NO$_2$ [M$^+$] 329, found [M+1]$^+$330.

4. Sulfonamide Formation Using P-HOBT

N-benzyl-p-toluenesulfonamide

To a suspension of P-HOBT 6 (1.01 g, 0.49 mmol) in CH$_2$Cl$_2$ (5 mL) was added p-toluenesulfonyl chloride (0.280 g, 1.47 mmol, 3.00 equiv.) and pyridine (0.155 g, 0.160 mL, 1.98 mmol, 4.04 equiv.). The suspension was subsequently rocked for 60 minutes at 25° C. The polymer was then filtered and washed with CH$_2$Cl$_2$ (3×5 mL), MeCN (3×5 mL), and MeOH (3×5 mL). The polymer was re-suspended in CH$_2$Cl$_2$ (5 mL), followed by the addition of benzylamine (0.026 g, 0.027 mL, 0.24 mmol, 0.49 equiv. based on P-HOBT 6). The suspension was rocked at 25° C. for 2 h. The polymer was then filtered and washed with CH$_2$Cl$_2$ (2×5 mL). The filtrate and washings were combined and concentrated to yield 0.050 g (77%) of N-benzyl-p-toluenesulfonamide as a light yellow crystalline solid.

$^1$H NMR (300 MHz, CDCl$_3$): δ 2.44 (s, 3H, CH$_3$), 4.14 (s, 2H, ArCH$_2$), 4.60 (bs, 1H, NH), 7.25 (m, 7H, ArH), 7.76 (m, 2H, ArH).

5. Acetylation of H$_2$N-MVTTD-COOH

AcHN-MVTTD-COOH

To a suspension of P-HOBT 3 (0.505 g, 0.19 mmol) in CH$_2$Cl$_2$ (5 mL) was added acetic anhydride (0.216 g, 0.200 mL, 2.12 mmol, 11 equiv.) and pyridine (0.234 g, 0.240 mL, 2.96 mmol, 16 equiv.). The suspension was subsequently rocked for 60 minutes at 25° C. The polymer was then filtered and washed with CH$_2$Cl$_2$ (2×5 mL), MeOH (3×5 mL), DMF (3×5 mL), and MeOH (3×5 mL). The polymer was re-suspended in phosphate buffer (0.05 M, pH 7.0, 5 mL), followed by the addition of H$_2$N-MVTTD-COOH TFA salt (prepared via standard solid phase peptide synthesis techniques, 0.0020g, 0.0029 mmol, 0.015 equiv. based on P-HOBT 3). The suspension was rocked at 25° C. for 5 h. The polymer was then filtered and washed with water (5 mL). The filtrate and washings were combined and lyophilized. RP-HPLC [Waters binary gradient chromatography system, Phenomenex Jupiter C$_{18}$ semi-prep reversed-phase column (10 mm×250 mm, 300 Å pore size, 5 m particle size, Phenomenex, Torrance, Calif., 30° C., 3 mL/min, 220 nm, 0–37.5% MeCN (0.1% TFA) over 20 min] of the reaction mixture indicated a 50% conversion of H$_2$N-MVTTD-COOH (retention time 12.8 min) to AcHN-MVTTD-COOH (retention time 15.7 min) with no other products present.

6. Fish and Meat Packaging Sensor for Detection of Spoilage

As raw fish and meat products spoil due to improper handling or age, chemically reactive amines are produced in relatively high concentrations. In particular, fish of the Scrombridae family (e.g., tuna, mackeral) and non-scromboid relatives (e.g., bluefish, mahi-mahi, amberjack) release histamine during bacterial degradation (i.e., spoilage). It is known that histamine causes scromboid poisoning, a form of food poisoning with severe symptoms, sometimes even death. The currently accepted FDA amine detection method in fish is based on organoleptic techniques (i.e., the use of smell). However, polymer bound 1-hydroxybenzotriazole-6-carboxylic acid can be used to detect the presence of amines with high sensitivity using absorbance (i.e., visible color change) or fluorescence detection methods.

Figure 6A:
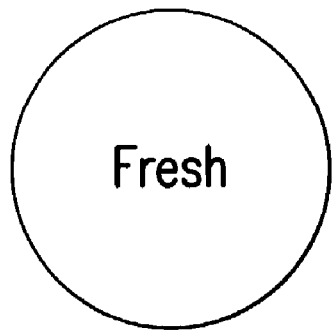
FIG. 6a is an illustration of the meat packaging sensor according to one aspect of the present invention showing that the food is safe for consumption.
Figure 6B:
FIG. 6b is an illustration of the meat packaging sensor according to one aspect of the present invention showing that the food is not safe for consumption.
Figure 7:
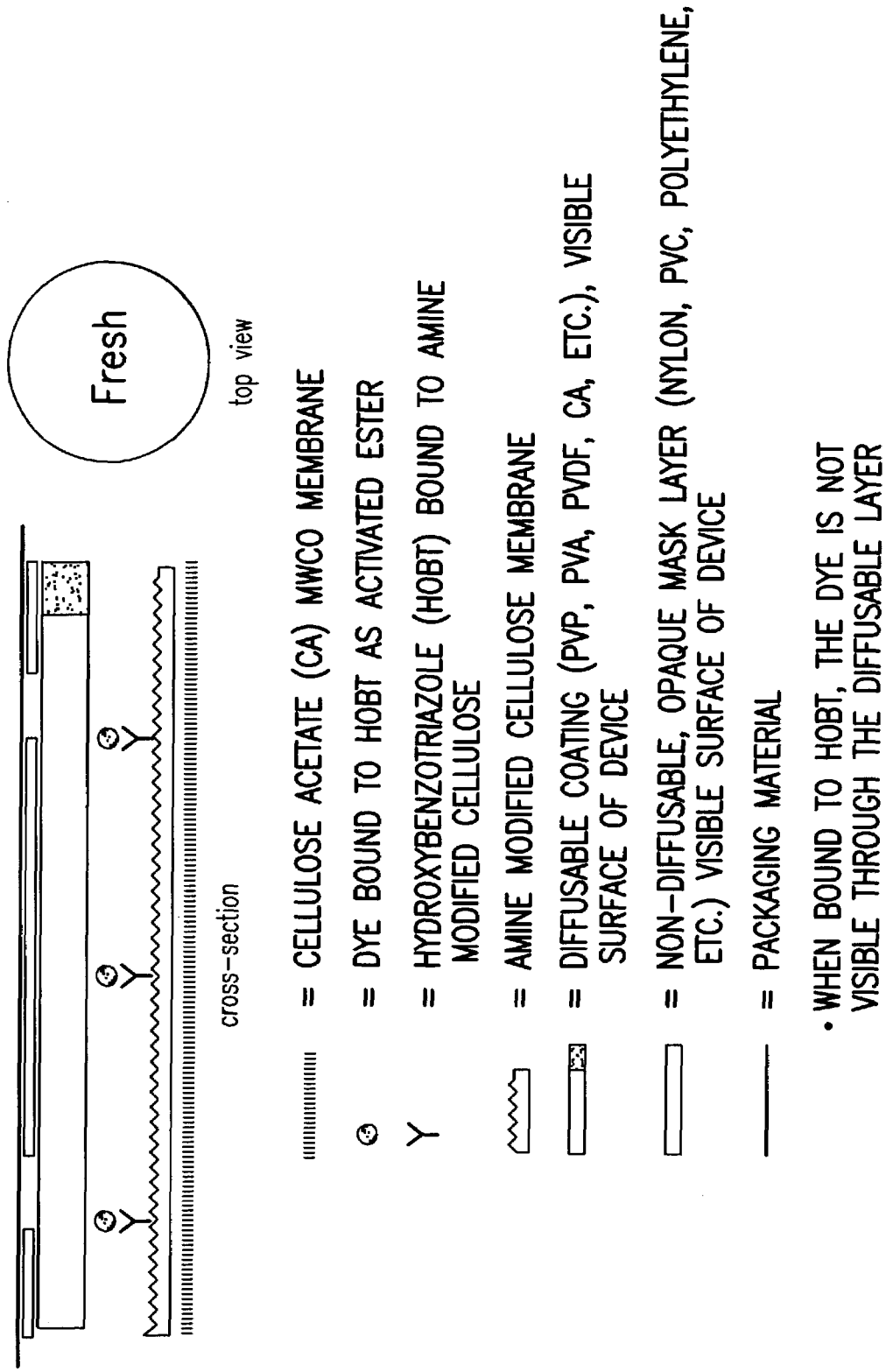
FIG. 7 is an illustration of the wafer sensor device according to one embodiment of the present invention.

In a preferred embodiment of the present invention, the polymer bound 1-hydroxybenzotriazole-6-carboxylic acid is utilized in the preparation of a disposable sensor for the detection of spoilage in packaged raw fish, meat, and poultry for consumer applications. The sensor includes a thin circular wafer which is placed in direct contact with the food of interest before the final wrapping is put in place. (See FIG. 7). In the absence of amines, the wafer remains white, indicating that the food is safe for consumers (see FIG. 6a). However, when amines are present, they react with the immobilized 1-hydroxybenzotriazole-6-carboxylic acid, thereby releasing an FDA approved dye which then becomes visible on the surface of the wafer. This color change indicates that the food is no longer safe for consumption (see FIG. 6b).

Figure 8:
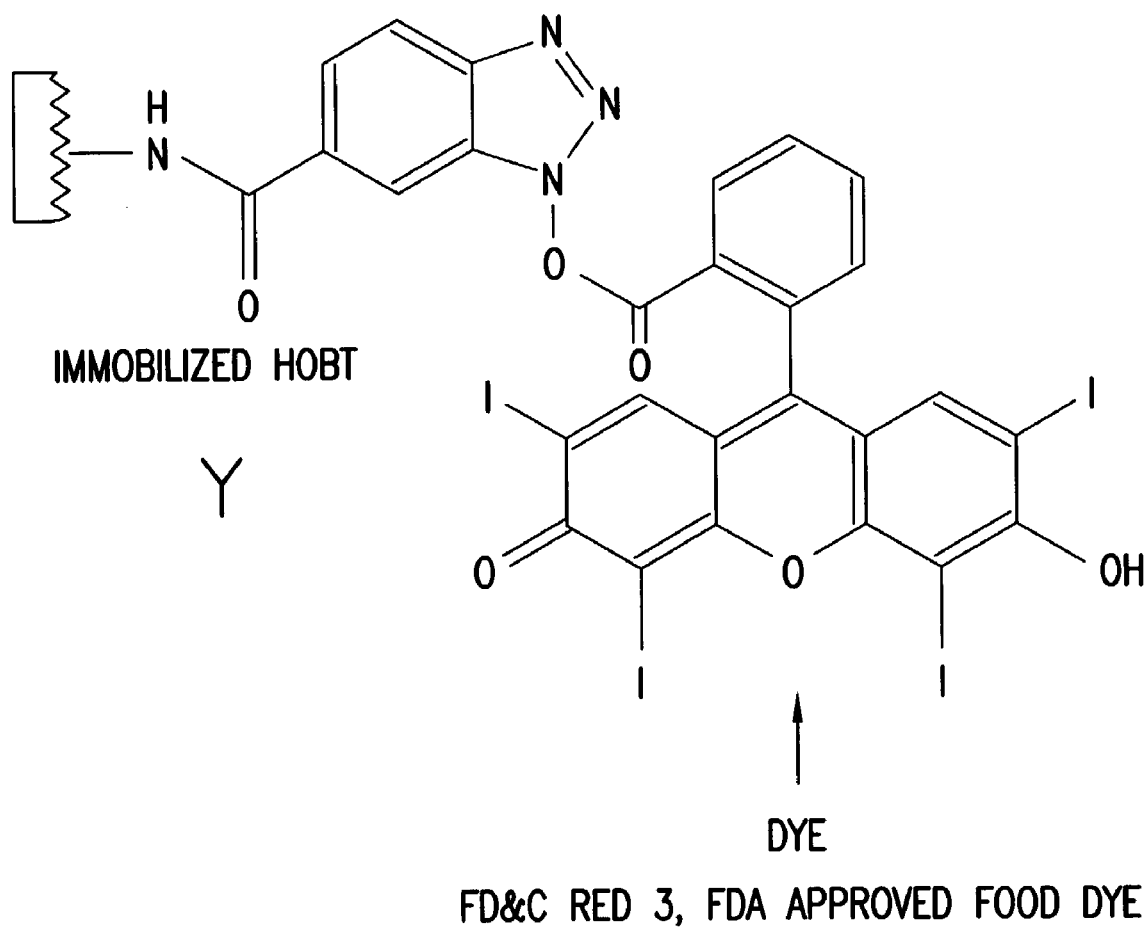
FIG. 8 is an illustration of the dye activated cellulose surface of the wafer sensor device according to one embodiment of the present invention.

The interface with the raw fish or meat product is a porous membrane having a pre-determined molecular weight cutoff (MWCO) which permits small molecules such as amines to pass, but will not allow intact cells, proteins, or other contaminants to pass. Suitable examples of the porous membrane include cellulose, cellulose acetate, PVDF, polypropylene, polyurethane, polyacrylonitrile, nitrocellulose, and polysulfone. A second layer, which is located adjacent to the porous membrane, is formed of a porous support to which 1-hydroxybenzotriazole-6-carboxylic acid is bound via amide bond formation on an amine modified support, or bound via an ester linkage to a free hydroxyl group. Suitable examples of supports include cellulose, cellulose acetate, polypropylene, polyurethane, chitosan, polyacrylonitrile, polysulfone, polyvinylalcohol, and modified derivatives thereof. The support may also include a hydroxyl group, a primary amine group, or a secondary amine group. Once immobilized, the HOBT derivative is modified with an FDA approved food dye (e.g., FD&C Red 3) via carbodiimide mediated ester formation to yield the activated reagent as shown in FIG. 8. Other dyes, including but not limited to, the azo dyes DABCYL and DABSYL may be utilized in the present invention.

The wafer is completed by the addition of a suitable diffusable layer which may be formed of polyvinylpyrrolidone, cellulose, cellulose acetate, PVDF, polypropylene, polyurethane, polyacrylonitrile, nitrocellulose, chitosan, polyvinylalcohol, or polysulfone. Other suitable examples would be easily determined by one of skill in the art. This layer serves as the visible surface of the device, as well as for the potential entrapment of co-reagents (e.g., to modify the environment in the sensor, such as pH) if necessary. A non-porous, opaque top layer, e.g., polyamide (e.g. Nylon), PVC, polystyrene, polypropylene, polyethylene or polyester, is utilized as a mask to yield the design as described in FIG. 6b. Once assembled, the wafer device is held together by sealing the perimeter with an FDA approved adhesive. After placement on the raw fish or meat surface, packaging material is placed over the wafer to hold the wafer in place on the surface of the meat product by pressure. Alternatively, an adhesive may be applied to the outer perimeter of the top exposed surface of the wafer to adhere it to the packaging material.

Figure 9A:
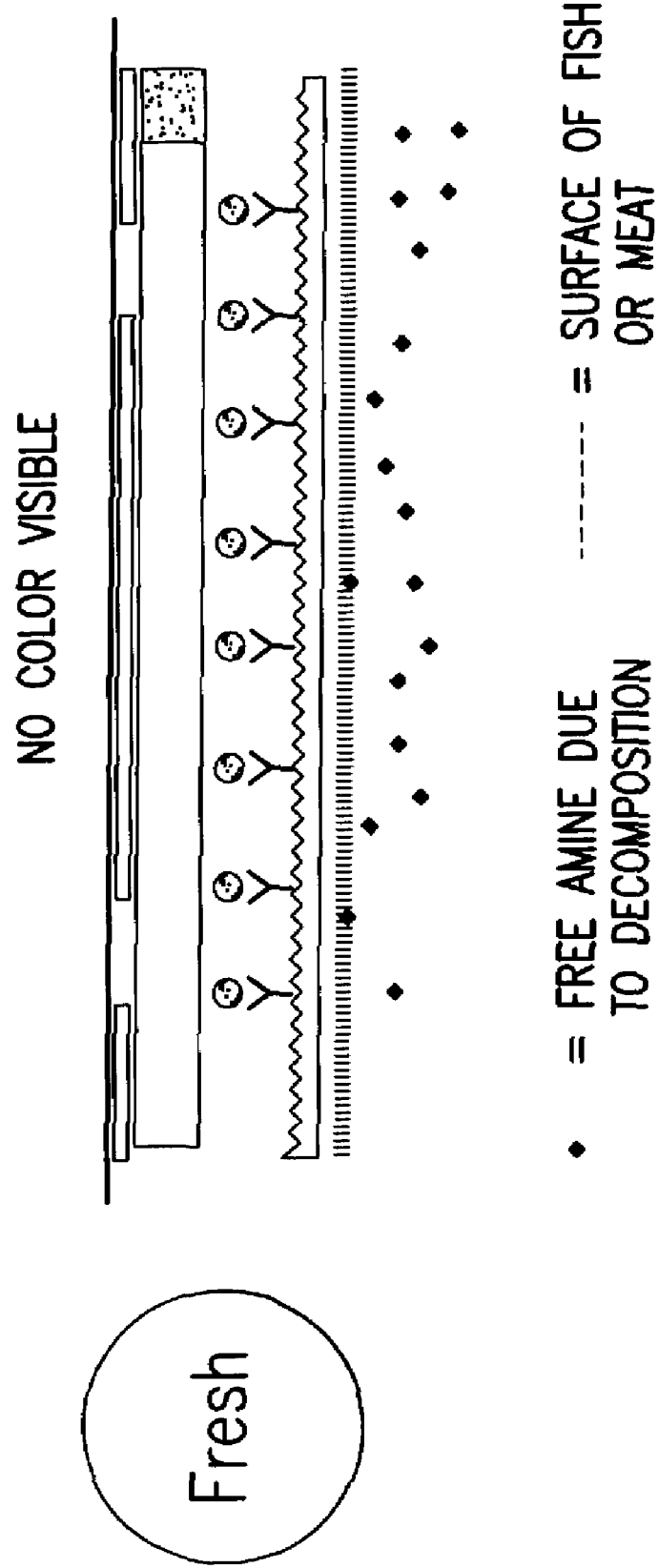
FIG. 9a is an illustration of the mode of action of the wafer sensor device according to one embodiment of the present invention when the meat product is fresh.
Figure 9B:
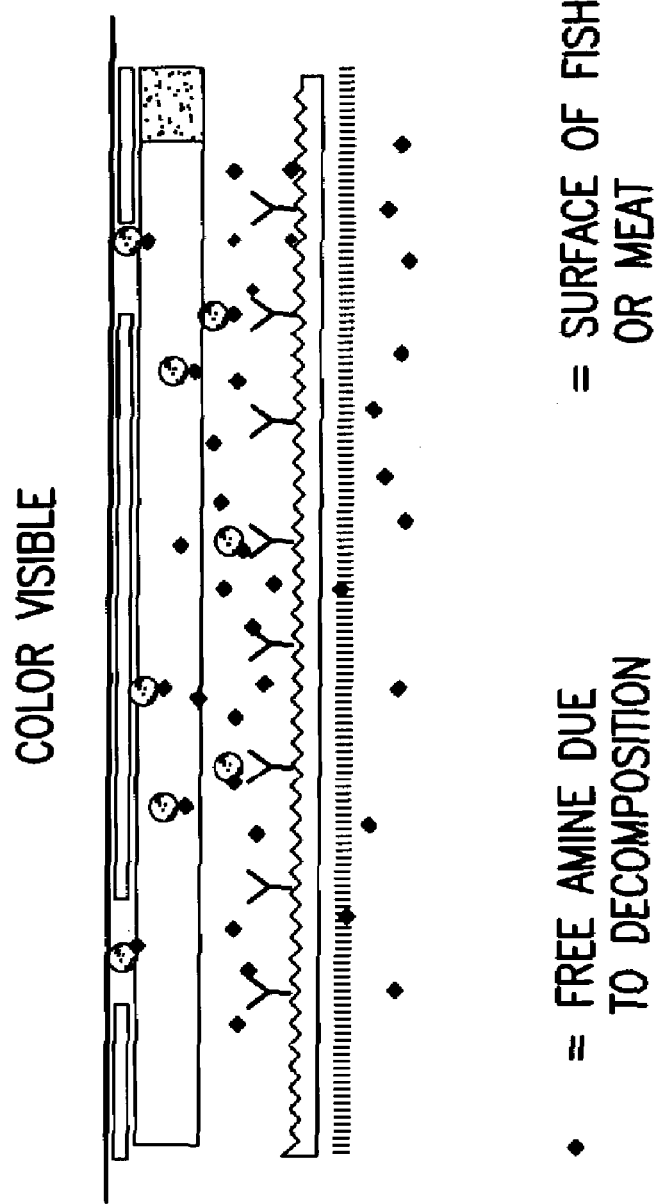
FIG. 9b is an illustration of the mode of action of the wafer sensor device according to one embodiment of the present invention when the meat product is spoiled.
Figure 9B:
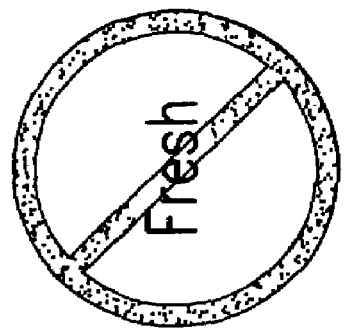
Figure 10:
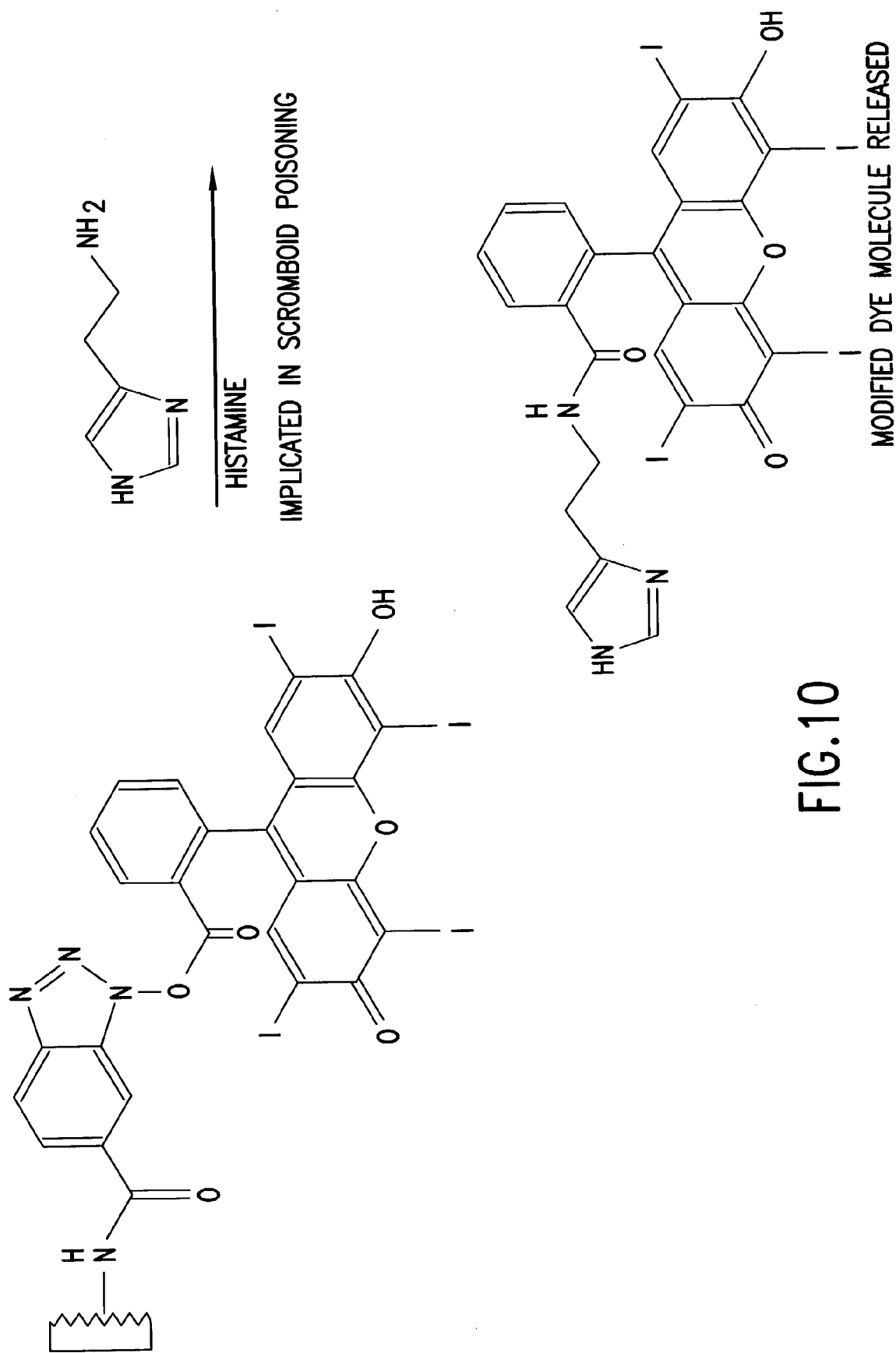
FIG. 10 is an illustration of the general chemistry involved in the release of the dye in the wafer sensor device according to one embodiment of the present invention.

Once in place, the wafer will function as shown in FIGS. 9a and 9b. In particular, when the meat is fresh, no amines are diffused through the cellulose acetate membrane. Consequently, no color is visible on the surface of the wafer, as shown in FIG. 9a. When the meat decomposes and spoils, amines are released. As shown in FIG. 9b, the amines pass through the porous MWCO membrane and react with the bound 1-hydroxybenzotriazole-6-carboxylic acid/dye conjugate, thereby releasing the modified dye. The modified dye then passes through the diffusable visible layer where color becomes visible in any unmasked areas. The intensity of the color change is proportional to the total amine concentration in the sample. Thus, a darker and more visible color indicates a more spoiled meat product.

7. Amine Diagnostic Kit for Detection of Food Spoilage

Figure 11:
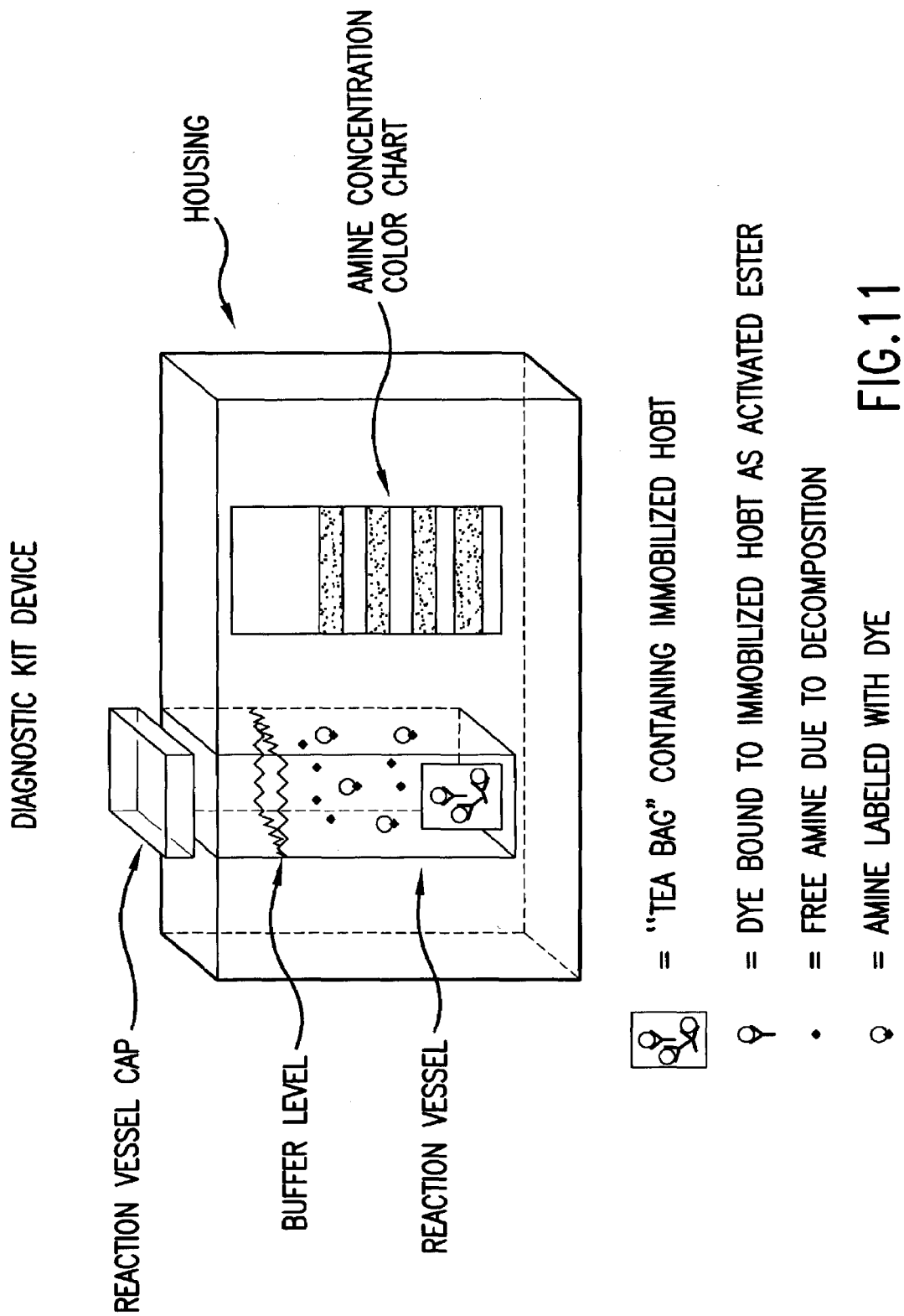
FIG. 11 is an illustration of the amine diagnostic kit according to one embodiment of the present invention.

In another preferred embodiment, the polymer bound 1-hydroxybenzotriazole-6-carboxylic acid may be utilized for the development of diagnostic reagents or kits which can be used both on-site (qualitative) and off-site (quantitative) for the detection of amines from food spoilage in wholesale environments (e.g., packing plants), retail environments, or for consumer applications. The diagnostic kit (see FIG. 11) includes a transparent reaction chamber, a color chart, packets of dye labeling agent, and an analysis buffer. The transparent reaction chamber is supplied with a snug fitting cap made of rigid plastic, such as polymethylmethacrylate (PMMA), polystyrene, or polyethylene. In a preferred embodiment, the kit is contained in a housing. The housing (see FIG. 11) can be molded or machined from a rigid plastic, including but not limited to polymethylmethacrylate (PMMA), polystyrene, and polyethylene. In a further preferred embodiment, the kit includes a "sample kit" which is used to obtain the sample of interest. The sample kit includes items such as cotton swabs, cellulose swipes, or filter paper swipes in a discrete package.

The dye labeling reagent may be in the form of "tea bag" or "test strip". For the "tea bag", 1-hydroxybenzotriazole-6-carboxylic acid is immobilized on a solid support in bead or powder form via amide bond formation on an amine modified support, or bound via an ester linkage to a free hydroxyl group. The "tea bag" is of suitable dimensions such that when it is filled with reagent it fits easily into the reaction chamber. The support includes, but is not limited to polystyrene, polystyrene/polyethylene glycol graft copolymers, silica gels, controlled pore glass, agarose, sepharose, and modified derivatives thereof. Additionally, the support may contain a hydroxyl group, a primary amine group, or a secondary amine group. Once immobilized, the HOBT derivative is modified with an FDA approved food dye (e.g., FD&C Red 3) via carbodiimide mediated ester formation to yield the activated reagent. Other dyes, including but not limited to, the azo dyes DABCYL and DABSYL, may also be utilized. The immobilized 1-hydroxybenzotriazole-6-carboxylic acid/dye conjugate is contained in the "tea bag". The "tea bag" material may be formed of filter paper, Nylon®, polyester, or cellulose. Other suitable examples will be easily determined by one of skill in the art. A single "tea bag" will be utilized for each analysis.

For the test strip dye labeling reagent, 1-hydroxybenzotriazole-6-carboxylic acid is immobilized on a rigid, porous solid support (i.e., the strip) via amide bond formation on an amine modified support, or bound via an ester linkage to a free hydroxyl group. The test strip is of suitable dimension such that when it is filled with reagent, it fits easily into the reaction chamber. Suitable supports include cellulose, cellulose acetate, polypropylene, polyurethane, chitosan, polyacrylonitrile, polysulfone, polyvinylalcohol and modified derivatives thereof. Additionally, the support may include a hydroxyl group, a primary amine group, or a secondary amine group. Once immobilized, the HOBT derivative is modified with an FDA approved food dye (e.g., FD&C Red 3) via carbodiimide mediated ester formation to yield the activated reagent. Other dyes, including but not limited to the azo dyes DABCYL and DABSYL, may be utilized. A single "test strip" will be utilized for each analysis.

The buffer for use in the kits according to the present invention may be individually or bulk prepackaged in powder form (dissolved in water before use) or in bulk solution. The buffer includes phosphate, carbonate, acetate, HEPES, Tris, or combinations thereof. Other examples can be easily determined by those of skill in the art. Modifiers, such as salts and chelating agents may also be added.

In use, a sample of the food of interest is obtained and added to the reaction chamber along with a packet of dye labeling agent and an appropriate amount of buffer. The reaction chamber is then closed and agitated for a finite period of time, after which time the dye labeling reagent is removed. The color of the resulting solution indicates degree of spoilage (i.e., total amine content) of the food. A sample may be taken from the solution for further quantitative analysis, such as by any known analytical methods, to determine the identity and concentration of the amines present in the food sample.

A specific usage of the amine diagnostic kit is described hereafter. For example, a sample of the food of interest (e.g., tuna fish) is obtained by swiping the food surface with a cotton swab. The swab is then dipped into the reaction chamber containing the buffer. The sample diffuses into buffer from the swab. The swab is then removed and a "tea bag" or "test strip" containing the immobilized HOBT is added to the reaction chamber. The reaction chamber is then closed and agitated for two minutes, after which the "tea bag" or "test strip" is removed. The color of the resulting solution indicates degree of spoilage (i.e., total amine content) of the food. In particular, the intensity of the color change is proportional to the total amine concentration in the sample, and is determined by comparison to the color chart. Thus, a darker and more visible color indicates a more spoiled food sample. A sample may be taken from the solution for further quantitative analysis, such as by known analytical methods, to determine the identity and concentration of the amines present in the food sample.

The invention of this application is described above both generically, and with regard to specific embodiments. A wide variety of alternatives known to those of ordinary skill in the art can be selected within the generic disclosure, and examples are not to be interpreted as limiting, unless specifically so indicated. The invention is not otherwise limited, except for the recitation of the claims set forth below. All references cited herein are incorporated in their entirety.

REFERENCES

1. "Combinatorial Chemistry: synthesis and application", Wilson, S. R., Czarnik, A. W., eds, Wiley, New York (1997).
2. "Combinatorial peptide and nonpeptide libraries: a handbook", Jung, G., ed., VCH, New York (1996).
3. "Solid phase organic synthesis notes" in "The Combinatorial Chemistry Catalog", NovaBiochem (1996).
4. "Solid phase peptide synthesis: a practical approach", Atherton, E., Sheppard, R. C., IRL Press, Oxford (1989).
5. "Oligonucleotide Synthesis: a practical approach", Gait, M. J., ed., IRL Press, Oxford (1984).
6. Rano et al, Tetrahedron Lett. 36:3789 (1995).
7. Deshpande, M. S., Tetrahedron Lett. 35:5613 (1994).
8. Forman et al., J. Org. Chem. 60:523 (1995).
9. Yu et al., Tetrahedron Lett., 35:8919 (1994).
10. Hiroshige et al., Tetrahedron Lett., 36:4567 (1995).
11. Chen et al., J. Am. Chem. Soc., 116:2661 (1994).
12. Bunin et al., J. Am. Chem. Soc., 114:10997 (1992).
13. Hobbs DeWitt et al., Proc. Natl. Acad. Sci. USA, 90:6909 (1993).
14. Hobbs DeWitt et al., Drug Dev. Res., 33:116 (1994).
15. Fridkin et al., J. Am. Chem. Soc., 87:4646 (1965).
16. Fridkin et al., J. Am. Chem. Soc., 88:3164 (1966).
17. Kalir et al., A. Eur. J. Biochem., 42:151 (1974).
18. Laufer et al., J. Am. Chem. Soc., 90:2696–2698 (1968).
19. Kalir et al., A. Eur. J. Biochem., 59:55–61 (1975).
20. Mokotoff et al., Int. J. Pept. Protein Res., 21:145 (1983).
21. Mokotoff et al., J. Med. Chem., 33:354 (1990).
22. Weinshenker et al., Tetrahedron Lett., 3281 (1972).
23. Desai et al., Tetrahedron Lett., 34:7685 (1993).
24. Arnold et al., J. Am. Chem. Soc., 111:3973 (1989).
25. Caputo et al., Synthesis, 141 (1995).
26. Pop et al., J. Org. Chem., 62:2594–2603 (1997).
27. Dendrinos, K. G. et al., J. Chem. Soc., Chem. Commun., 499–500 (1998).
28. Huang et al., Tetrahedron Lett., 36:9113–9116 (1995).
29. Dendrinos et al., Tetrahedron Lett., 39:1321–1324 (1998).
30. Dendrinos et al., J. Chem. Soc., Perkins Trans. I, 1463–1464 (198).
31. König et al., Chem. Ber., 103:788 (1970).
32. Nuclear Magnetic Resonance Spectra, Sadtler Research Laboratories, Inc., 28971 M (1975).
33. Imrie et al., J. Org. Chem., 58:5643–5649 (1993).
34. Kishikawa et al., Synthesis, 173–175 (1994).
35. Morcuende et al., J. Org. Chem., 61:5264–5270 (1996).
36. Kita et al., J. Org. Chem., 51:4150–4158 (1986).
37. Richards et al., Tetrahedron, 39:3549–3568 (1983).
38. "The Aldrich Library of $^{13}$C and $^1$H FT-NMR Spectra", Pouchert, C. J., Behnke, J., Aldrich Chemical Co., I(2): 1385A (1992).

What is claimed is:

1. An indicator for detecting the presence of amines in a sample comprising:
    a releasable indicator bound to a compound linked to a solid support;
    wherein in the presence of amines, said indicator is released, thereby causing a detectable change; and
    wherein said change is proportional to the amount of amines present in said sample wherein said compound linked to said solid support is represented by the following formula:

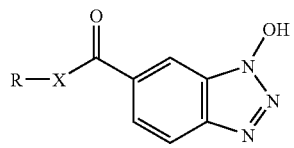

wherein X represents O, S or NR$^1$, wherein R$^1$ is H or an alkyl group; and
wherein R represents said solid support selected from the group consisting of silica gels, silica beads, chitosan, cellulose, cellulose acetate, glass beads, controlled pore glass, agarose, sepharose and modified derivatives thereof, and wherein the releaseable indicator comprises an azo dye linked to the compound through the hydroxy moiety on the compound.

2. The indicator of claim 1, wherein said releaseable indicator is selected from the group consisting of DABCYL and DABSYL.

3. An indicator for detecting the presence of amines in a sample comprising:
    a releasable indicator bound to a compound linked to a solid support;
    wherein in the presence of amines, said indicator is released, thereby causing a detectable change; and
    wherein said change is proportional to the amount of amines present in said sample wherein said compound linked to said solid support is represented by the following formula:

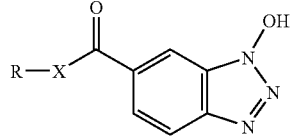

wherein X represents O, S or NR$^1$, wherein R$^1$ is H or an alkyl group; and
wherein R represents said solid support selected from the group consisting of silica gels, silica beads, chitosan cellulose, cellulose acetate, glass beads, controlled pore glass, agarose, sepharose and modified derivatives thereof,
and wherein the releaseable indicator comprises FD&C Red 3 linked to the compound through the hydroxy moiety on the compound.

4. A method for detecting the presence of amines in a sample comprising:

placing a porous flow through device containing a releasable indicator bound to a compound linked to a solid support into a transparent reaction vessel; and adding said sample to said reaction vessel;

wherein when said sample passes through said flow through device, amines present in said sample cause the release of said releasable indicator, thereby causing a visible color change; and wherein said color indicates the presence of amines in said sample, wherein said compound linked to said solid support is represented by the following formula:

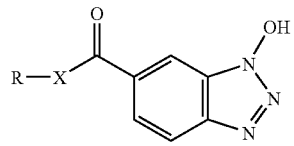

wherein X represents a divalent linker moiety or NR$^1$, wherein R$^1$ is H or an alkyl group; and wherein R represents said solid support, and wherein the compound bears a dye linked to the compound through the hydroxy moiety on the compound.

5. The method of claim 4, wherein said flow through device is a porous bag.

6. The method of claim 4, wherein said reaction vessel is a test tube or cuvette.

7. The method of claim 4, wherein said dye is an azo dye.

8. The method of claim 7, wherein said azo dye is selected from the group consisting of DARCYL and DABSYL.

9. The method of claim 4, wherein the intensity of the color change is proportional to the amount of amines in said sample.

10. The method of claim 4, wherein the dye comprises FD&C Red 3.

11. A device for detecting the presence of amines in a sample comprising:

a first layer including a compound linked to a solid support that permits the passage of amines, wherein said compound linked to said solid support is represented by the following formula:

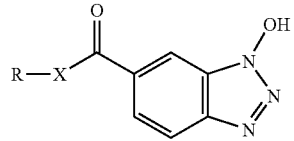

wherein X represents a divalent linker moiety or NR$^1$, wherein R$^1$ is H or an alkyl group and R represents said solid support, said compound further bearing a dye linked to said compound through the hydroxy moiety on the compound; and a coating layer through which said dye may diffuse overlaying said first layer;

wherein when said amines pass through said first layer, said amines react with said dye-bearing compound, thereby releasing said dye, said dye then diffusing through said coating layer to form a visible color change on said coating layer; and wherein said color change on said coating layer indicates the presence of amines in said sample.

12. The device of claim 11, further comprising a second layer underlying said first layer, said second layer comprising a porous membrane that permits the passage of amines.

13. The device of claim 12, wherein said porous membrane is selected from the group consisting of cellulose, cellulose acetate, PVDF, polypropylene, polyurethane, polyacrylonitrile, nitrocellulose and polysulfone.

14. The device of claim 11, further comprising a non-porous, opaque masking layer overlaying said coating layer, said masking layer being impermeable to said dye, wherein said masking layer limits the portions of said coating layer which may be visible.

15. The device of claim 14, wherein said masking layer is selected from the group consisting of polyamide, PVC, polystyrene, polypropylene, polyethylene and polyester.

16. The device of claim 11, wherein said solid support is selected from the group consisting of cellulose, cellulose acetate, polypropylene, polyurethane, chitosan, polyacrylonitrile, polysulfone, polyvinyl alcohol and modified derivatives thereof.

17. The device of claim 11, wherein said dye is selected from the group consisting of FD&C Red 3, DABCYL and DABSYL.

18. The device of claim 11, wherein said coating layer is selected from the group consisting of polyvinylpyrrolidone, cellulose, cellulose acetate, PVDF, polypropylene, polyurethane, polyacrylonitrile, nitrocellulose, chitosan, polyvinyl alcohol and polysulfone.

19. The method claim 11, wherein the intensity of the color change is proportional to the amount of amines present in said sample.

20. A method of detecting the presence of amines in a sample comprising:

placing the device of claim 11 on a sample; and observing a color change when amines are present.

21. The method of claim 20, wherein said sample is meat, fish, or poultry.

22. The method of claim 21, wherein packaging material is placed over said device to hold said device on said sample.

23. The method of claim 22, wherein said device is affixed to said packaging material by an adhesive.

24. A compound directly linked to a solid support, wherein said compound linked to said solid support is represented by the following formula:

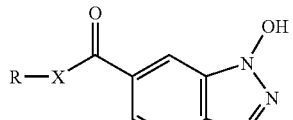

wherein X represents O, S or NR$^1$, wherein R$^1$ is H or an alkyl group; and wherein R represents said solid support selected from the group consisting of silica gels, silica beads, chitosan, cellulose, cellulose acetate, glass beads, controlled pore glass, agarose, sepharose and modified derivatives thereof, and wherein said compound bears a detectable agent comprising FD&C Red 3, DABCYL, DABSYL, pyrene, fluorescein, lucifer yellow, BODIPY, rhodamine, DANSYL, EDANS, $^3$H, $^{14}$C, $^{125}$I, $^{35}$S, or $^{32}$P, linked to the compound through the hydroxy moiety on the compound.

25. A compound directly linked to a solid support, wherein said compound linked to said solid support is represented by the following formula:

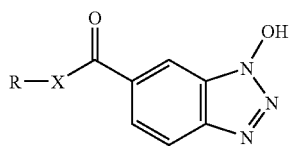

wherein X represents O, S or NR$^1$, wherein R$^1$ is H or an alkyl group; and wherein R represents said solid support selected from the group consisting of silica gels, silica beads, chitosan, cellulose, cellulose acetate, glass beads, controlled pore glass, agarose, sepharose and modified derivatives thereof, and wherein said compound bears a detectable agent comprising an electrochemical agent that contains a thiol or catechol moiety.

26. A flow through device for amino group modification of a substrate comprising a housing containing a compound linked to a solid support, wherein said compound linked to said solid support is represented by the following formula:

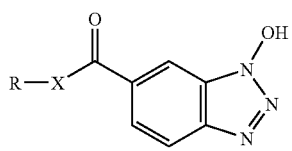

wherein X represents a divalent linker moiety or NR$^1$, wherein R$^1$ is H or an alkyl group;

wherein R represents said solid support; and wherein said housing includes an inlet and an outlet; and wherein said compound bears a detectable agent selected from the group consisting of a chromophoric agent, a fluorogenic agent, a radioactive agent and an electrochemical agent linked to the compound through the hydroxy moiety on the compound.

27. The flow through device of claim 26, wherein said housing is selected from the group consisting of a cartridge, a syringe and a column.

28. The flow through device of claim 26, wherein said device is disposable.

29. The flow through device of claim 26, wherein said device further comprises a collection vessel.

30. The flow through device of claim 26, wherein said detectable agent is selected from the group consisting of FD&C Red 3, DABCYL, DABSYL, pyrene, fluorescein, lucifer yellow, BODIPY, rhodamine, DANSYL, EDANS, $^3$H, $^{14}$C, $^{125}$I, $^{35}$S, $^{32}$P.

31. The flow through device of claim 26, wherein the electrochemical agent contains a thiol or catechol moiety.

32. The flow through device of claim 26, wherein said support is selected from the group consisting of polystyrene, polystyrene/polyethylene glycol graft copolymers, silica gel, controlled pore glass, agarose, sepharose, cellulose acetate, polypropylene, polyurethane, chitosan, polyacrylonitirle, polysulfone and polyvinylalcohol.

33. The flow through device of claim 26, wherein said amino group modification is selected from the group consisting of the formation of amides, the formation of carbamates and the formation of sulfonamides.

34. The flow through device of claim 26, wherein said substrate is selected from the group consisting of proteins, peptides, and amines.

35. A method for amino group modification of a substrate comprising:

adding said substrate to be modified to the device of claim 26;

passing said substrate through said device, wherein when said substrate comes into contact with said compound, a chemical reaction occurs between said substrate and said compound, thereby modifying said substrate; and collecting said modified substrate.

36. The method of claim 35, further comprising the step of wetting said flow through device with a solvent prior to adding said substrate to said device.

37. The method of claim 35, wherein said chemical reaction is an acylation or sulfonylation reaction.

38. The method of claim 35, wherein said amino group modification is selected from the group consisting of the formation of amides, the formation of carbamates and the formation of sulfonamides.

39. A kit for detecting the presence of amines in a sample comprising:

a transparent reaction chamber;

a color chart based on known amine concentration standards; and a compound directly linked to a solid support, wherein said compound linked to said solid support is represented by the following formula:

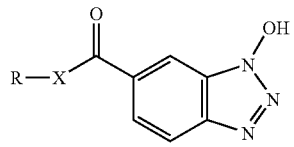

wherein X represents a divalent linker moiety or NR$^1$, wherein R$^1$ is H or an alkyl group;

wherein R represents said solid support; and wherein said compound further bears a dye linked to the compound through the hydroxy moiety on the compound.

40. The kit according to claim 39, wherein said compound is contained in a porous membrane.

41. The kit according to claim 40, wherein said porous membrane is selected from the group consisting of filter paper, polyester and cellulose.

42. The kit according to claim 39, wherein said compound is immobilized on a rigid, porous support.

43. The kit according to claim 42, wherein said support is selected from the group consisting of cellulose, cellulose acetate, polypropylene, polyurethane, chitosan, polyacrylonitrile, polysulfone, polyvinylalcohol and modified derivatives thereof; said support including a member selected from the group consisting of a hydroxyl group, a primary amine group and a secondary amine group.

44. The kit according to claim 39, wherein said support is selected from the group consisting of polystyrene, polystyrene/polyethylene glycol graft copolymers, silica gels, controlled pore glass, agarose, sepharose and modified derivatives thereof.

45. The kit according to claim 39, wherein said dye is an azo dye.

46. The kit according to claim 45, wherein said azo dye is selected from the group consisting of DABCYL and DABSYL.

47. The kit according to claim 39, further comprising a buffer.

48. The kit according to claim 47, wherein said buffer is selected from the group consisting of phosphate, acetate, HEPES, Tris and combinations thereof.

49. The kit of claim 39, wherein the dye comprises FD&C Red 3.

* * * * *